US008853455B2

(12) United States Patent
Korte et al.

(10) Patent No.: US 8,853,455 B2
(45) Date of Patent: Oct. 7, 2014

(54) PROCESS FOR PREPARING SUBSTITUTED 2-NITROBIPHENYLS

(75) Inventors: Alexander Korte, Neustadt (DE); Jan Klaas Lohmann, Mannheim (DE); Thomas Grote, Wachenheim (DE); Klaus Ebel, Lampertheim (DE); Thomas Zierke, Boehl-Iggelheim (DE); Horst Mayer, Ludwigshafen (DE); Ralf Wazulek, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 68 days.

(21) Appl. No.: 13/254,946

(22) PCT Filed: Mar. 8, 2010

(86) PCT No.: PCT/EP2010/052914
§ 371 (c)(1),
(2), (4) Date: Sep. 6, 2011

(87) PCT Pub. No.: WO2010/102980
PCT Pub. Date: Sep. 16, 2010

(65) Prior Publication Data
US 2011/0319665 A1 Dec. 29, 2011

(30) Foreign Application Priority Data
Mar. 9, 2009 (EP) .................................... 09154619

(51) Int. Cl.
C07C 211/00 (2006.01)
C07C 209/00 (2006.01)
C07C 205/11 (2006.01)
C07C 205/10 (2006.01)
C07C 205/09 (2006.01)

(52) U.S. Cl.
CPC ........... *C07C 205/11* (2013.01); *C07C 2101/16* (2013.01); *C07C 205/10* (2013.01); *C07C 205/09* (2013.01)
USPC .......................................... 564/307; 564/416

(58) Field of Classification Search
None
See application file for complete search history.

(56) References Cited

U.S. PATENT DOCUMENTS

| 5,866,513 | A | 2/1999 | Michelotti et al. |
| 8,343,637 | B2 | 1/2013 | Parham et al. |
| 2007/0185149 | A1 | 8/2007 | Kautz |

FOREIGN PATENT DOCUMENTS

| CA | 2 694 636 | 2/2009 |
| CN | 1594278 | 3/2005 |
| CN | 101374799 | 2/2009 |
| DE | 10 2007 002 714 | 7/2008 |
| WO | WO 2007/138089 | 12/2007 |

OTHER PUBLICATIONS

International Search Report prepared in International Application No. PCT/EP2010/052914, filed Mar. 8, 2010.
International Preliminary Report on Patentability from corresponding International Application No. PCT/EP2010/052914, filed Mar. 8, 2010.
Allen, C.F.H. et al., "The diene synthesis with β-nitrostyrene", Journal of Organic Chemistry, (1943), pp. 373-379, vol. 8, Search Report.
Barluenga, J. et al., "Easy preparation of 2-Methyl-1, 3-Dimorpholino-1, 3-Butadiene and an overview of its synthetic applications", Tetrahedron Letters, (1995), pp. 6551-6554, Search Report.
Berestoviskaya et al., "Title", Zhurnal Organicheskoi Khimii, (1980), pp. 891-892, vol. 16, No. 4, Search Report.
Bradsher, C. et al., "2-Iodo-4'-chlorobiphenyl", (1946), Journal of the American Chemical Chemistry, (1946), pp. 404-405, vol. 68, Search Report.
Murase, M. et al., "A new and reactive Diels-Alder Diene, N, N-Dimethylamino-3-Methylthiobutadiene", Chemical and Pharmaceutical Bulletin, (1992), pp. 1343-1345, vol. 40, No. 5, Search Report.
Neher, M. et al., "Chloronitrostyrenes in the Diels-Alder reaction", Journal of Organic Chemistry, (1961), pp. 5220-5221, vol. 26, Search Report.
Oida, T. et al., "The Diels-Alder reaction of N, N-Diethyl-1, 3-butadienylamine with several β-substituted styrenes and use of the reaction products for the one-pot synthesis of 2-substituted biphenyls", Bulletin of the Institute for Chemical Research, (1982), pp. 336-341, vol. 60, No. 5-6, Search Report.
Shastin, A. V. et al., "New synthetic approach to α-fluoro-β-arylvinyl sulfones and their application in Diels-Alder reactions", Tetrahedron, (2008), pp. 9725-9732, vol. 64, No. 41, Search Report.
Berestovitskaya, V.M., et al., "Synthesis and Structure of Phosphorylated Nitrocyclohexenes", Russian Journal of General Chemistry 2007,, p. 25-35, vol. 77, No. 1.
Bordwell, Frederick G., et al., "Reactions of Carbanions with Electron Acceptors", Journal of Organic Chemistry, Apr. 19, 1985, p. 1151-1156, vol. 50, No. 8.
Ayerbe, Mirari, et al., "4M Lithium perchlorate-nitromethane: an efficient solvent in diels-alder reactions using nitroalkenes as dienophiles", Tetrahedron Letters, 1995, p. 4447-4450, vol. 36, No. 25.

*Primary Examiner* — Clinton Brooks
(74) *Attorney, Agent, or Firm* — Brinks Gilson & Lione

(57) ABSTRACT

The present invention relates to a process for preparing substituted 2-nitrobiphenyls and to specific 2-nitrobiphenyls. The invention further relates to a process for preparing 2-aminobiphenyls from such 2-nitrobiphenyls and to a process for preparing (het)arylamides of such 2-aminobiphenyls.

27 Claims, No Drawings

PROCESS FOR PREPARING SUBSTITUTED 2-NITROBIPHENYLS

This application is a National Stage application of International Application No. PCT/EP2010/052914, filed Mar. 8, 2010, the entire contents of which is hereby incorporated herein by reference. This application also claims priority under 35 U.S.C. §119 to European Patent Application No. 09154619.2 filed Mar. 9, 2009, the entire contents of which is hereby incorporated herein by reference.

The present invention relates to a process for preparing substituted 2-nitrobiphenyls and to specific 2-nitrobiphenyls. The invention further relates to a process for preparing 2-aminobiphenyls from such 2-nitrobiphenyls and to a process for preparing (het)arylamides of such 2-aminobiphenyls.

Functionalized biphenyl compounds are of great interest especially as pharmaceuticals and pesticides, and as precursors of such active ingredients. For their synthesis, a series of organometallic methods is available, which offer efficient access to a multitude of biphenyl derivatives. However, organometallic methods are also afflicted by some disadvantages. For instance, their attractiveness is reduced by high costs, especially in the case of palladium-catalyzed reactions, lack of environmental compatibility, as in the case of nickel, and low maturity, especially in the case of catalysis with cobalt and iron compounds.

Ring-substituted 2-nitrobiphenyls are important precursors for aryl- and heteroarylcarboxamides which find use as fungicides, and for which boscalid is a prominent representative.

It was an object of the present invention to provide an easily performable process for preparing ring-substituted 2-nitrobiphenyls and for preparing (het)arylcarboxamides derived from 2-aminobiphenyls which in turn are prepared from such 2-nitrobiphenyls. This process should additionally be performable inexpensively and avoid the use of expensive organometallic reagents, especially of transition metal catalysts.

The object is achieved by the processes described in detail below.

The present invention provides a process for producing 2-nitrobiphenyl compounds of formula I

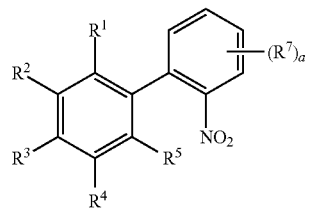

(I)

wherein
$R^1$, $R^2$, $R^3$, $R^4$ and $R^5$ are independently of each other selected from hydrogen, halogen, cyano, hydroxyl, $C_1$-$C_6$-alkyl, wherein the alkyl group may carry 1, 2 or 3 substituents $R^6$; $C_1$-$C_6$-haloalkyl, $C_3$-$C_{10}$-cycloalkyl which may carry 1, 2, 3 or 4 $C_1$-$C_4$-alkyl substituents; $C_3$-$C_{10}$-halocycloalkyl; $C_1$-$C_6$-alkoxy, $C_1$-$C_6$-haloalkoxy, $C_1$-$C_6$-alkylthio, $C_1$-$C_6$-haloalkylthio, $C_1$-$C_6$-alkylcarbonyl, $C_1$-$C_6$-haloalkylcarbonyl, $C_1$-$C_6$-alkoxycarbonyl, $C_1$-$C_6$-haloalkoxycarbonyl, aryl; aryl-$C_1$-$C_4$-alkyl; arylcarbonyl; aryl-$C_1$-$C_4$-alkylcarbonyl; aryloxycarbonyl; aryl-$C_1$-$C_4$-alkoxycarbonyl, wherein aryl in the six last-mentioned radicals may carry 1, 2, 3 or 4 substituents selected from halogen, $C_1$-$C_4$-alkyl, $C_1$-$C_4$-haloalkyl and a radical $R^6$; aminocarbonyl; $C_1$-$C_4$-alkylaminocarbonyl and di-($C_1$-$C_4$-alkyl)-aminocarbonyl; or $R^1$ and $R^2$ or $R^2$ and $R^3$ or $R^3$ and $R^4$ or $R^4$ and $R^5$, together with the carbon atoms to which they are bound, form a 5- or 6-membered partially unsaturated or aromatic carbocyclic or heterocyclic ring, where the heterocyclic ring contains 1, 2, 3 or 4 heteroatoms selected from N, O and S as ring members;
each $R^6$ is independently selected from $C_3$-$C_{10}$cycloalkyl which may carry 1, 2, 3 or 4 $C_1$-$C_4$-alkyl substituents; $C_3$-$C_{10}$-halocycloalkyl; $C_1$-$C_4$-alkoxy; $C_1$-$C_4$-haloalkoxy; amino; $C_1$-$C_4$-alkylamino; di-($C_1$-$C_4$-alkyl)-amino; carboxyl; hydroxyl; SH and aryl;
each $R^7$ is independently selected from $C_1$-$C_4$-alkyl, $OR^8$, amino, $C_1$-$C_4$-alkylamino, di-($C_1$-$C_4$-alkyl)-amino and halogen (preferably fluorine);
where
$R^8$ is selected from hydrogen, $C_1$-$C_4$-alkyl, aryl, wherein aryl may carry 1, 2, 3 or 4 substituents selected from halogen, $C_1$-$C_4$-alkyl, $C_1$-$C_4$-haloalkyl and a radical $R^6$; and a protecting group; and
a is 0, 1 or 2;
comprising reacting a compound of formula II

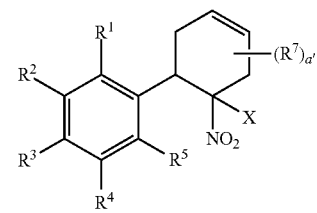

(II)

wherein $R^1$, $R^2$, $R^3$, $R^4$, $R^5$ and $R^7$ are as defined above, a' is 0, 1 or 2 and X is a halogen atom,
with a base
and, if necessary, aromatizing the resulting product.

This process is referred to hereinafter as process A.

The reaction of compound II with a base is an elimination reaction, to be more precise a dehydrohalogenation.

As a matter of course, in compounds II (and also in the later-described compounds III, X.1 and X.2) in which a' is 2, the two substituents $R^7$ are not bound to the same carbon atom. In compounds II, III and X.1 in which a' is 1 or 2, the substituent(s) $R^7$ is/are not bound to the carbon atom carrying the phenyl substituent. Moreover, in compounds III in which a' is 1 or 2, the substituent(s) $R^7$ is/are not bound to the carbon atom carrying the nitro group, neither.

The invention also relates to a process for preparing 2-aminobiphenyl compounds of formula VI

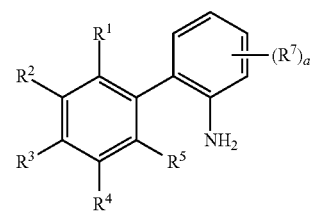

(VI)

wherein $R^1$, $R^2$, $R^3$, $R^4$, $R^5$, $R^7$ and a are as defined above, comprising following elimination and aromatization step (step (i)) and reduction step (step (ii)):

(i) reacting a compound of formula II as defined above with a base, if necessary aromatizing the resulting product and obtaining a compound of formula I as defined above; and
(ii) reacting the compound of formula I obtained in step (i) with a reduction agent.

This process is referred to hereinafter as process B.

The invention further relates to a process for preparing N-acyl-2-aminobiphenyls of the general formula (VII)

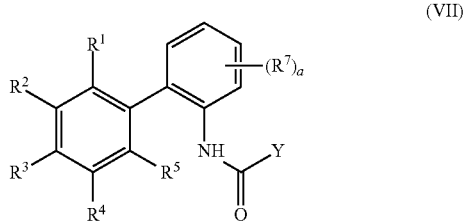

(VII)

wherein
$R^1$, $R^2$, $R^3$, $R^4$, $R^5$, $R^7$ and a are as defined above; and
Y is aryl or 5- or 6-membered hetaryl having 1, 2, 3 or 4 heteroatoms which are selected from N, O and S as ring members, where aryl and hetaryl optionally bear 1, 2, 3 or 4 substituents which are selected from halogen, $C_1$-$C_4$-alkyl, $C_1$-$C_4$-haloalkyl, $C_1$-$C_4$-alkoxy and $C_1$-$C_4$-haloalkoxy,
comprising following elimination, aromatization, reduction and acylation steps:
(i) reacting a compound of formula II as defined above with a base, if necessary aromatizing the resulting product and obtaining a compound of formula I as defined above;
(ii) reacting the compound of formula I obtained in step (i) with a reduction agent and obtaining a compound of formula VI as defined above; and
(iii) N-acylating the compound of the formula (VI) obtained in step (ii) by reacting it with a compound of the general formula (VIII),

(VIII)

wherein Y is as defined above; and
W is a leaving group.

This process is referred to hereinafter as process C.

In the context of the present invention, the terms used generically are defined as follows:

The prefix $C_x$—$C_y$ denotes the number of possible carbon atoms in the particular case.

The term "halogen" denotes in each case fluorine, bromine, chlorine or iodine, especially fluorine, chlorine or bromine.

The term "$C_1$-$C_4$-alkyl" denotes a linear or branched alkyl radical comprising from 1 to 4 carbon atoms, such as methyl, ethyl, propyl, 1-methylethyl (isopropyl), butyl, 1-methylpropyl (sec-butyl), 2-methylpropyl (isobutyl) or 1,1-dimethylethyl (tert-butyl).

The term "$C_1$-$C_6$-alkyl" denotes a linear or branched alkyl radical comprising from 1 to 6 carbon atoms, Examples encompass, apart those already mentioned for $C_1$-$C_4$-alkyl, pentyl, hexyl and positional isomers thereof.

The term "$C_1$-$C_{10}$-alkyl" denotes a linear or branched alkyl radical comprising from 1 to 10 carbon atoms. Examples are, apart those already mentioned for $C_1$-$C_6$-alkyl, heptyl, octyl, 2-ethylhexyl, nonyl, decyl, 2-propylheptyl and positional isomers thereof.

The term "$C_1$-$C_4$-haloalkyl", as used herein and in the haloalkyl units of $C_1$-$C_4$-haloalkoxy, describes straight-chain or branched alkyl groups having from 1 to 4 carbon atoms, where some or all of the hydrogen atoms of these groups have been replaced by halogen atoms. Examples thereof are chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 3,3,3-trifluoroprop-1-yl, 1,1,1-trifluoroprop-2-yl, 3,3,3-trichloroprop-1-yl, heptafluoroisopropyl, 1-chlorobutyl, 2-chlorobutyl, 3-chlorobutyl, 4-chlorobutyl, 1-fluorobutyl, 2-fluorobutyl, 3-fluorobutyl, 4-fluorobutyl and the like.

The term "$C_1$-$C_6$-haloalkyl", as used herein and in the haloalkyl units of $C_1$-$C_6$-haloalkoxy, describes straight-chain or branched alkyl groups having from 1 to 6 carbon atoms, where some or all of the hydrogen atoms of these groups have been replaced by halogen atoms. Examples thereof are, apart those mentioned above for $C_1$-$C_4$-haloalkyl, 1-chloropentyl, 2-chloropentyl, 3-chloropentyl, 4-chloropentyl, 5-chloropentyl, 1-fluoropentyl, 2-fluoropentyl, 3-fluoropentyl, 4-fluoropentyl, 5-fluoropentyl and the like.

The term "$C_1$-$C_4$-alkoxy" denotes straight-chain or branched saturated alkyl groups comprising from 1 to 4 carbon atoms, which are bonded via an oxygen atom. Examples of $C_1$-$C_4$-alkoxy are methoxy, ethoxy, n-propoxy, 1-methylethoxy (isopropoxy), n-butoxy, 1-methylpropoxy (sec-butoxy), 2-methylpropoxy (isobutoxy) and 1,1-dimethylethoxy (tert-butoxy).

The term "$C_1$-$C_6$-alkoxy" denotes straight-chain or branched saturated alkyl groups comprising from 1 to 6 carbon atoms, which are bonded via an oxygen atom. Examples are, apart those mentioned above for $C_1$-$C_4$-alkoxy, pentyloxy, hexyloxy and positional isomers thereof.

The term "$C_1$-$C_4$-haloalkoxy" describes straight-chain or branched saturated haloalkyl groups comprising from 1 to 4 carbon atoms, which are bonded via an oxygen atom. Examples thereof are chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, 1,1,2,2-tetrafluoroethoxy, 1-chloro-1,2,2-trifluoroethoxy, pentafluoroethoxy, 3,3,3-trifluoroprop-1-oxy, 1,1,1-trifluoroprop-2-oxy, 3,3,3-trichloroprop-1-oxy, 1-chlorobutoxy, 2-chlorobutoxy, 3-chlorobutoxy, 4-chlorobutoxy, 1-fluorobutoxy, 2-fluorobutoxy, 3-fluorobutoxy, 4-fluorobutoxy and the like.

The term "$C_1$-$C_6$-haloalkoxy" describes straight-chain or branched saturated haloalkyl groups comprising from 1 to 6 carbon atoms, which are bonded via an oxygen atom. Examples thereof are, apart those mentioned above for $C_1$-$C_4$-haloalkoxy, 1-chloropentoxy, 2-chloropentoxy, 3-chloropentoxy, 4-chloropentoxy, 5-chloropentoxy, 1-fluoropentoxy, 2-fluoropentoxy, 3-fluoropentoxy, 4-fluoropentoxy, 5-fluoropentoxy and the like.

The term "$C_1$-$C_4$-alkylthio" denotes straight-chain or branched saturated alkyl groups comprising from 1 to 4 carbon atoms, which are bonded via a sulfur atom. Examples of $C_1$-$C_4$-alkylthio are methylthio, ethylthio, n-propylthio, 1-methylethylthio (isopropylthio), n-butylthio, 1-methylpropylthio (sec-butylthio), 2-methylpropylthio (isobutylthio) and 1,1-dimethylethylthio (tert-butylthio).

The term "$C_1$-$C_6$-alkylthio" denotes straight-chain or branched saturated alkyl groups comprising from 1 to 6 carbon atoms, which are bonded via a sulfur atom. Examples are, apart those mentioned above for $C_1$-$C_4$-alkylthio, pentylthio, hexylthio and positional isomers thereof.

The term "$C_1$-$C_4$-haloalkylthio" describes straight-chain or branched saturated haloalkyl groups comprising from 1 to 4 carbon atoms, which are bonded via a sulfur atom. Examples thereof are chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, 1,1,2,2-tetrafluoroethylthio, 1-chloro-1,2,2-trifluoroethylthio, pentafluoroethylthio, 3,3,3-trifluoroprop-1-ylthio, 1,1,1-trifluoroprop-2-ylthio, 3,3,3-trichloroprop-1-ylthio, 1-chlorobutylthio, 2-chlorobutylthio, 3-chlorobutylthio, 4-chlorobutylthio, 1-fluorobutylthio, 2-fluorobutylthio, 3-fluorobutylthio, 4-fluorobutylthio and the like.

The term "$C_1$-$C_6$-haloalkylthio" describes straight-chain or branched saturated haloalkyl groups comprising from 1 to 6 carbon atoms, which are bonded via a sulfur atom. Examples thereof are, apart those mentioned above for $C_1$-$C_4$-haloalkylthio, 1-chloropentylthio, 2-chloropentylthio, 3-chloropentylthio, 4-chloropentylthio, 5-chloropentylthio, 1-fluoropentylthio, 2-fluoropentylthio, 3-fluoropentylthio, 4-fluoropentylthio, 5-fluoropentylthio and the like.

The term "$C_1$-$C_4$-alkylcarbonyl" denotes alkyl radicals having from 1 to 4 carbon atoms which are bonded via a carbonyl group. Examples thereof are methylcarbonyl (acetyl), ethylcarbonyl, propylcarbonyl, isopropylcarbonyl, n-butylcarbonyl, sec-butylcarbonyl, isobutylcarbonyl and tert-butylcarbonyl.

The term "$C_1$-$C_6$-alkylcarbonyl" denotes alkyl radicals having from 1 to 6-carbon atoms which are bonded via a carbonyl group. Examples thereof are, apart those mentioned above for $C_1$-$C_4$-alkylcarbonyl, pentylcarbonyl, hexylcarbonyl and positional isomers thereof.

The term "$C_1$-$C_4$-haloalkylcarbonyl" denotes haloalkyl radicals having from 1 to 4 carbon atoms which are bonded via a carbonyl group. Examples thereof are fluoromethylcarbonyl, difluoromethylcarbonyl, trifluoromethylcarbonyl, 1-fluoroethylcarbonyl, 2-fluoroethylcarbonyl, 1,1-difluoroethylcarbonyl, 2,2-difluoroethylcarbonyl, 2,2,2-trifluoroethylcarbonyl, pentafluoroethylcarbonyl and the like.

The term "$C_1$-$C_6$-haloalkylcarbonyl" denotes haloalkyl radicals having from 1 to 6 carbon atoms which are bonded via a carbonyl group. Examples thereof are, apart those mentioned above for $C_1$-$C_6$-haloalkylcarbonyl, 1-chloropentylcarbonyl, 2-chloropentylcarbonyl, 3-chloropentylcarbonyl, 4-chloropentylcarbonyl, 5-chloropentylcarbonyl, 1-fluoropentylcarbonyl, 2-fluoropentylcarbonyl, 3-fluoropentylcarbonyl, 4-fluoropentylcarbonyl, 5-fluoropentylcarbonyl and the like.

The term "$C_1$-$C_4$-alkoxycarbonyl" denotes alkoxy radicals having from 1 to 4 carbon atoms which are bonded via a carbonyl group. Examples thereof are methoxycarbonyl, ethoxycarbonyl, propoxycarbonyl, isopropoxycarbonyl, n-butoxycarbonyl, sec-butoxycarbonyl, isobutoxycarbonyl and tert-butoxycarbonyl.

The term "$C_1$-$C_6$-alkoxycarbonyl" denotes alkoxy radicals having from 1 to 6 carbon atoms which are bonded via a carbonyl group. Examples thereof are, apart those mentioned above for $C_1$-$C_4$-alkoxycarbonyl, pentoxycarbonyl, hexoxycarbonyl and the positional isomers thereof.

The term "$C_1$-$C_4$-haloalkoxycarbonyl" denotes haloalkoxy radicals having from 1 to 4 carbon atoms which are bonded via a carbonyl group. Examples thereof are fluoromethoxycarbonyl, difluoromethoxycarbonyl, trifluoromethoxycarbonyl, 1-fluoroethoxycarbonyl, 2-fluoroethoxycarbonyl, 1,1-difluoroethoxycarbonyl, 2,2-difluoroethoxycarbonyl, 2,2,2-trifluoroethoxycarbonyl, pentafluoroethoxycarbonyl and the like.

The term "$C_1$-$C_6$-haloalkoxycarbonyl" denotes haloalkoxy radicals having from 1 to 6 carbon atoms which are bonded via a carbonyl group. Examples thereof are, apart those mentioned above for $C_1$-$C_6$-alkoxycarbonyl, 1-chloropentoxycarbonyl, 2-chloropentoxycarbonyl, 3-chloropentoxycarbonyl, 4-chloropentoxycarbonyl, 5-chloropentoxycarbonyl, 1-fluoropentoxycarbonyl, 2-fluoropentoxycarbonyl, 3-fluoropentoxycarbonyl, 4-fluoropentoxycarbonyl, 5-fluoropentoxycarbonyl and the like.

The term "aryl" denotes carbocyclic aromatic radicals having from 6 to 14 carbon atoms. Examples thereof comprise phenyl, naphthyl, fluorenyl, azulenyl, anthracenyl and phenanthrenyl. Aryl is preferably phenyl or naphthyl, and especially phenyl.

The term "hetaryl" denotes aromatic radicals having from 1 to 4 heteroatoms which are selected from O, N and S as ring members. Examples thereof are 5- and 6-membered hetaryl radicals having 1, 2, 3 or 4 heteroatoms selected from O, S and N as ring members, such as pyrrolyl, furanyl, thienyl, pyrazolyl, imidazolyl, oxazolyl, isoxazolyl, thiazolyl, isothiazolyl, triazolyl, tetrazolyl, pyridyl, pyrazinyl, pyridazinyl, pyrimidyl and triazinyl.

The term "arylcarbonyl" denotes aryl radicals which are bonded via a carbonyl group. Examples thereof are phenylcarbonyl (benzoyl), and naphthylcarbonyl.

The term "aryl-$C_1$-$C_4$-alkyl" denotes aryl radicals which are bonded via a $C_1$-$C_4$-alkyl group. Examples thereof are benzyl, 2-phenylethyl (phenethyl) and the like.

The term "aryloxy" denotes a radical of formula Ar—O—, where Ar is an aryl radical. Examples thereof are phenoxy and naphthoxy.

The term "aryloxycarbonyl" denotes a radical of formula Ar—O—CO—, where Ar is an aryl radical. Examples thereof are phenoxycarbonyl and naphthoxycarbonyl.

The term "aryl-$C_1$-$C_4$-alkylcarbonyl" denotes aryl radicals which are bonded via a $C_1$-$C_4$-alkylcarbonyl group. Examples thereof are benzylcarbonyl and 2-phenylethylcarbonyl.

The term "aryl-$C_1$-$C_4$-alkoxycarbonyl" denotes aryl radicals which are bonded via a $C_1$-$C_4$-alkoxycarbonyl group. Examples thereof are benzyloxycarbonyl and fluorenylmethoxycarbonyl.

The protective group $R^8$ can be any group suitable for protecting the oxygen atom of an OH group. Examples are benzyl, silyl protective groups, such as trimethylsilyl (TMS), tert-butyldimethylsilyl (TBDMS) or tert-butyldiphenylsilyl (TBDPS), carbonyl protective groups, such as 2,2,2-trichloroethoxycarbonyl (TROC), or tetrahydropyranyl.

The remarks made below regarding preferred embodiments of the processes according to the invention, especially regarding preferred embodiments of the radicals of the different reactants and products and of the reaction conditions of the processes according to the invention, apply either taken alone or, more particularly, in any conceivable combination with one another. The remarks regarding preferred embodiments apply to processes A, B and C of the invention, as far as they overlap and if not specified otherwise.

The reactions described herein are carried out in reaction vessels customary for such reactions, the reaction being configurable continuously, semicontinuously or batchwise.

Preferably, and for each occurrence, $R^1$, $R^2$, $R^3$, $R^4$ and $R^5$ are independently of each other selected from hydrogen; halogen; cyano; hydroxyl; $C_1$-$C_6$-alkyl, wherein the alkyl group may carry 1, 2 or 3 substituents $R^6$; $C_1$-$C_6$-haloalkyl; $C_3$-$C_{10}$-cycloalkyl which may carry 1, 2, 3 or 4 $C_1$-$C_4$-alkyl substituents; $C_3$-$C_{10}$-halocycloalkyl; $C_1$-$C_6$-alkoxy; $C_1$-$C_6$-haloalkoxy; $C_1$-$C_6$-alkylthio; $C_1$-$C_6$-haloalkylthio; aryl; aryl-$C_1$-$C_4$-alkyl; wherein aryl in the two last-mentioned radicals may carry 1, 2, 3 or 4 substituents selected from halogen, $C_1$-$C_4$-alkyl, $C_1$-$C_4$-haloalkyl and a radical $R^6$ which is different from carboxyl; amino; $C_1$-$C_4$-alkylamino and di-($C_1$-$C_4$-alkyl)-amino, more preferably from hydrogen, hydroxyl, halogen, $C_1$-$C_6$-alkyl, $C_1$-$C_6$-haloalkyl, $C_1$-$C_6$-alkoxy and $C_1$-$C_6$-haloalkoxy, even more preferably from hydrogen and halogen and in particular from hydrogen, fluorine and chlorine.

Preferably, $R^1$ and $R^5$ are hydrogen. More preferably, $R^1$ and $R^5$ are hydrogen and $R^2$, $R^3$ and $R^4$ are independently of each other selected from hydrogen, halogen, $C_1$-$C_6$-alkyl, $C_1$-$C_6$-haloalkyl, $C_1$-$C_6$-alkoxy and $C_1$-$C_6$-haloalkoxy and preferably from hydrogen and halogen, specifically hydrogen, fluorine and chlorine. In particular, $R^1$, $R^2$, $R^4$ and $R^5$ are hydrogen and $R^3$ is halogen, specifically chlorine; or $R^1$ and $R^5$ are hydrogen and $R^2$, $R^3$ and $R^4$ are halogen, specifically fluorine; or $R^1$, $R^2$ and $R^5$ are hydrogen and $R^3$ and $R^4$ are halogen, specifically chlorine. Specifically, $R^1$, $R^2$, $R^4$ and $R^5$ are hydrogen and $R^3$ is halogen, specifically chlorine, or $R^1$ and $R^5$ are hydrogen and $R^2$, $R^3$ and $R^4$ are halogen, specifically fluorine.

If $R^8$ is a protective group, this is preferably selected from benzyl, silyl protective groups, such as trimethylsilyl (TMS), tert-butyldimethylsilyl (TBDMS) or tert-butyldiphenylsilyl (TBDPS), carbonyl protective groups, such as 2,2,2-trichloroethoxycarbonyl (TROC), and tetrahydropyranyl. More preferably, a protective group $R^8$ is selected from silyl protective groups, in particular from trimethylsilyl (TMS) and tert-butyldimethylsilyl.

$R^8$ is preferably $C_1$-$C_4$-alkyl or a protective group, more preferably $C_1$-$C_4$-alkyl or a silyl protective group, even more preferably $C_1$-$C_4$-alkyl, trimethylsilyl or tert-butyldimethylsilyl, especially preferably methyl, ethyl, trimethylsilyl or tert-butyldimethylsilyl, in particular methyl or ethyl and specifically methyl.

Preferably, $R^7$ is selected from $C_1$-$C_4$-alkyl, $OR^8$, amino, $C_1$-$C_4$-alkylamino and di-($C_1$-$C_4$-alkyl)-amino. More preferably, $R^7$ is selected from $C_1$-$C_4$-alkyl, amino, methylamino, dimethylamino and a group $OR^8$; even more preferably from $C_1$-$C_4$-alkyl, amino, methylamino, dimethylamino and a group $OR^8$, where $R^8$ is preferably selected from $C_1$-$C_4$-alkyl, trimethylsilyl and tert-butyldimethylsilyl (i.e. the group $OR^8$ is preferably selected from $C_1$-$C_4$-alkoxy, trimethylsilyloxy and tert-butyldimethylsilyloxy), and particularly preferably from methyl, dimethylamino and a group $OR^8$, where $R^8$ is preferably selected from $C_1$-$C_4$-alkyl, preferably methyl or ethyl, trimethylsilyl and tert-butyldimethylsilyl (i.e. the group $OR^8$ is preferably selected from $C_1$-$C_4$-alkoxy, preferably methoxy or ethoxy, trimethylsilyloxy and tert-butyldimethylsilyloxy). In particular, $R^7$ is methyl, methoxy or ethoxy and is specifically methyl or methoxy.

To be more precise, $R^7$ in compounds of formulae I, VI and VII is preferably selected from $C_1$-$C_4$-alkyl, amino, methylamino, dimethylamino and a group $OR^8$, where $R^8$ is preferably a protective group which in turn is preferably trimethylsilyl or tert-butyldimethylsilyl. More preferably, $R^7$ in compounds of formulae I, VI and VII is selected from methyl, dimethylamino and a group $OR^8$, where $R^8$ is preferably a protective group which in turn is preferably trimethylsilyl or tert-butyldimethylsilyl. Specifically, $R^7$ in compounds of formulae I, VI and VII is methyl.

In case $R^8$ in compounds of formulae I, VI and VII is $C_1$-$C_4$-alkyl, the respective substituent(s) $OR^8$ is/are preferably bound in 3- and/or 4-position with respect to the 1-position of the phenyl substituent.

$R^7$ in compound II (and also in compounds III, IX, X.1 and X.2; see below) is preferably selected from $C_1$-$C_4$-alkyl, amino, methylamino, dimethylamino and a group $OR^8$; more preferably from $C_1$-$C_4$-alkyl, amino, methylamino, dimethylamino and a group $OR^8$, where the group $OR^8$ is preferably selected from $C_1$-$C_4$-alkoxy, trimethylsilyloxy and tert-butyldimethylsilyloxy, even more preferably from methyl, dimethylamino and a group $OR^8$, where the group $OR^8$ is preferably selected from $C_1$-$C_4$-alkoxy, preferably methoxy or ethoxy, trimethylsilyloxy and tert-butyldimethylsilyloxy. In particular, $R^7$ in compound II (and also in compounds III, IX, X.1 and X.2) is methyl, methoxy or ethoxy and is specifically methyl or methoxy.

In an alternatively preferred embodiment, $R^7$ in compound II (and also in compound III; see below) is preferably selected from halogen. In this case, a in the resulting compound I (and of course also VI and VII) is preferably (a'-1) and more preferably 0 with a' being 1.

a is 0, 1 or 2, preferably 0 or 1 and more preferably 0.

a' is 0, 1 or 2, preferably 0 or 1 and more preferably 0.

In compounds of formula II, X is preferably Cl, Br or I and in particular Cl or Br.

For the elimination step (i.e. the reaction of the compound of formula II with a base under elimination of HX=dehydrohalogenation), virtually all bases are suitable which under the given reaction conditions have a basicity sufficient for dehydrohalogenating compound II. Moreover, the base should of course not interfere with the elimination reaction. Suitable bases are inorganic or organic bases.

Suitable inorganic bases comprise alkali metal hydroxides, such as lithium, sodium or potassium hydroxide, earth alkaline metal hydroxides, such as magnesium or calcium hydroxide, alkali metal carbonates, such as lithium, sodium or potassium carbonate, and earth alkaline metal carbonates, such as magnesium or calcium carbonate. Mixtures of these bases can also be used. Preferred inorganic bases are alkali metal hydroxides, such as lithium, sodium or potassium hydroxide.

Suitable organic bases comprise alkali metal $C_1$-$C_4$-alkoxides, such as sodium methoxide, potassium methoxide, sodium ethoxide, potassium ethoxide, sodium propoxide, potassium propoxide, sodium isopropoxide, potassium isopropoxide, sodium butoxide, potassium butoxide, sodium tert-butoxide and potassium tert-butoxide, organic aliphatic amines, such as methylamine, dimethylamine, trimethylamine, ethylamine, diethylamine, triethylamine, propylamine, dipropylamine, tripropylamine, diisopropylethylamine, butylamine, dibutylamine and tributylamine, organic aliphatic alkanolamines, such as ethanolamine, diethanolamine and triethanolamine, cyclic amidines, such as 1,8-diazabicyclo[5.4.0]undec-7-en (DBU) and 1,5-diazabicyclo

[4.3.0]non-5-ene (DBN), and basic, saturated, partially unsaturated or aromatic heteromono- or bicyclic rings containing at least one nitrogen ring atom and 5 to 10 ring members, such as pyrrolidine, pyrazolidine, imidazolidine, oxazolidine, isoxazolidine, thiazolidine, isothiazolidine, piperidine, piperazine, pyridine, lutidine, picoline, 1,4-diazabicyclo[2.2.2]octane (DABCO) and the like. Mixtures of these bases can also be used. Preferred organic bases are alkali metal $C_1$-$C_4$-alkoxides, such as sodium methoxide, potassium methoxide, sodium ethoxide, potassium ethoxide, sodium propoxide, potassium propoxide, sodium isopropoxide, potassium isopropoxide, sodium butoxide, potassium butoxide, sodium tert-butoxide and potassium tert-butoxide. More preferred are sodium tert-butoxide and potassium tert-butoxide and in particular potassium tert-butoxide.

Preferably, an organic base is used. Preferred organic bases are alkali metal $C_1$-$C_4$-alkoxides, such as sodium methoxide, potassium methoxide, sodium ethoxide, potassium ethoxide, sodium propoxide, potassium propoxide, sodium isopropoxide, potassium isopropoxide, sodium butoxide, potassium butoxide, sodium tert-butoxide and potassium tert-butoxide. More preferred are sodium tert-butoxide and potassium tert-butoxide and in particular potassium tert-butoxide.

The compound II and the base are preferably used in a molar ratio of from 1:1 to 1:10. More preferably, the base is used in molar excess, i.e. from >1:1 to 1:10, such as 1:1.1 to 1:10 or 1:1.5 to 1:10, even more preferably from 1:1.5 to 1:5 and in particular from 1:1.5 to 1:3.

The elimination step is generally carried out in a solvent. Suitable solvents are chosen so as to dissolve at least partially the reactants, i.e. compound II and the base. Of course the solvent is not to negatively interfere with the elimination reaction.

In case an inorganic base is used, and thus a base which is scarcely soluble in most organic solvents, it is preferred to carry out the elimination reaction in a biphasic solvent system, more preferably in a solvent system comprising water and at least one organic solvent which is essentially immiscible with water under the given reaction conditions. "Essentially immiscible with water" means in this context that under the given reaction conditions (especially under the given reaction temperature) at most 10 g, preferably at most 5 g of the solvent are soluble in 100 g of water or, vice versa, that at most 10 g, preferably at most 5 g of water are soluble in 100 g of this solvent.

Examples of suitable solvents essentially immiscible with water are aliphatic hydrocarbons, such as pentane, hexane, heptane, octane and petroleum ether, cycloaliphatic hydrocarbons, such as cyclohexane and cyclooctane, chlorinated alkanes, such as dichloromethane, chloroform, tetrachloromethane, dichloroethylene and trichloroethylene, aromatic hydrocarbons, such as benzene, toluene and the xylenes, aliphatic ethers, such as diethylether, dipropylether, dibutylether, methyl-tert-butylether and methyl-isopropylether, and esters of aliphatic monocarboxylic acids, such as ethylacetate, propylacetate, ethylpropionate and propylpropionate. Preferred solvents are the above-mentioned aromatic hydrocarbons. Specifically, toluene is used.

Such a biphasic solvent system preferably also comprises at least one phase transfer catalyst. Suitable phase transfer catalysts are sufficiently well known to those skilled in the art and comprise, for example, charged systems such as organic ammonium salts, for example tetra($C_1$-$C_{18}$-alkyl)ammonium chlorides or bromides, such as tetramethylammonium chloride or bromide, tetrabutylammonium chloride or bromide, hexadecyltrimethylammonium chloride or bromide, octadecyltrimethylammonium chloride or bromide, methyltrihexylammonium chloride or bromide, methyltrioctylammonium chloride or bromide or benzyltrimethylammonium hydroxide (Triton B), and also tetra-($C_1$-$C_{18}$-alkyl)phosphonium chlorides or bromides such as tetraphenylphosphonium chloride or bromide, [(phenyl)$_m$-($C_1$-$C_{18}$-alkyl)$_n$]phosphonium chlorides or bromides in which m=from 1 to 3 and n=from 3 to 1 and the sum of m+n=4, and additionally pyridinium salts such as methylpyridinium chloride or bromide, and uncharged systems such as crown ethers or aza crown ethers, for example 12-crown-4, 15-crown-5, 18-crown-6, dibenzo-18-crown-6 or [2,2,2]-cryptand (222-Kryptofix), cyclodextrins, calixarenes such as [1$_4$]-metacyclophane, calix[4]arene and p-tert-butyl-calix[4]arene, and cyclophanes.

Preference is given to the use of the above-mentioned tetra($C_1$-$C_{18}$-alkyl)ammonium chlorides or bromides.

Alternatively, in case an inorganic base is used, the elimination reaction may also be carried out in at least one polar solvent, preferably at least one polar protic solvent.

Polar (protic and aprotic) solvents comprise $C_1$-$C_4$-alcohols, such as methanol, ethanol, propanol, isopropanol, butanol, sec-butanol, isobutanol and tert-butanol, glycols, such as ethylene glycol and propylene glycol, glycol ethers, such as diethylene glycol and triethylene glycol, $C_3$-$C_4$-ketones, such as acetone and ethylmethylketone, cyclic ethers, such as tetrahydrofuran and dioxane, amides, such as dimethylformamide (DMF) and dimethylacetamide, and dimethylsulfoxide.

Polar protic solvents comprise $C_1$-$C_4$-alcohols, such as methanol, ethanol, propanol, isopropanol, butanol, sec-butanol, isobutanol and tert-butanol, glycols, such as ethylene glycol and propylene glycol, and glycol ethers, such as diethylene glycol and triethylene glycol. Preference is given to the above-mentioned alcohols, $C_1$-$C_3$-alcohols (i.e. methanol, ethanol, propanol and isopropanol) being more preferred.

However, in case an inorganic base is used, the use of a biphasic solvent system is preferred for the elimination reaction.

In case an organic base is used, and thus a base which is at least partly soluble in some organic solvents, it is preferred to carry out the elimination reaction in a suitable organic solvent. In case the organic base is liquid under the given reaction conditions, it is possible to use the base itself as a solvent.

In case of the preferably used alkali metal $C_1$-$C_4$-aralkoxides, the organic solvents are preferably selected from polar and more preferably from polar-aprotic solvents. However, the above-mentioned chlorinated alkanes, especially dichloromethane or dichloroethylene, may be used, too.

Polar (protic and aprotic) solvents comprise $C_1$-$C_4$-alcohols, such as methanol, ethanol, propanol, isopropanol, butanol, sec-butanol, isobutanol and tert-butanol, glycols, such as ethylene glycol and propylene glycol, glycol ethers, such as diethylene glycol and triethylene glycol, $C_3$-$C_4$-ketones, such as acetone and ethylmethylketone, cyclic ethers, such as tetrahydrofuran and dioxane, amides, such as dimethylformamide (DMF) and dimethylacetamide, and dimethylsulfoxide.

Polar protic solvents are listed above.

Polar aprotic solvents comprise $C_3$-$C_4$-ketones, such as acetone and ethylmethylketone, cyclic ethers, such as tetrahydrofuran and dioxane, amides, such as dimethylformamide (DMF) and dimethylacetamide, and dimethylsulfoxide.

The elimination reaction is preferably carried out at a temperature of from 0° C. to the boiling point of the reaction mixture, more preferably from 20° C. to the boiling point of the reaction mixture.

Due to the reaction with the base, HX is eliminated from compound II (dehydrohalogenation). If the dehydrohalogenation is the fastest reaction step under the given condition, this formally first results in a cyclohexadiene compound (e.g. in a compound of formula X.1 or X.2, see below). This cyclohexadiene compound must be aromatized, for example by oxidation, in order to obtain the desired compound I.

However, if compound II carries a group $R^7$ (a'≠0) which under the reaction conditions of the elimination reaction can also eliminate (of course together with a hydrogen atom bound to a vicinal carbon atom of the cyclohexene ring), the elimination may directly yield the biphenyl compound I wherein a=a'−1. In this case, a specific, separate aromatization step is not necessary (this is meant by the term "if necessary" aromatizing the resulting product in process A and in step (i) of processes B and C; see also below). Groups $R^7$ which may eliminate under the above described reaction conditions are for example $C_1$-$C_4$-alkoxy groups ($R^7$=$OR^8$, wherein $R^8$=$C_1$-$C_4$-alkyl) and especially methoxy, aryloxy groups ($R^7$=$OR^8$, wherein $R^8$=aryl) or, in particular, halogen ($R^7$=halogen). Moreover, group $R^7$ shall not be bound to a carbon atom of the cyclohexene double bond. Thus, if the compound II carries one group $R^7$ in said positions which is a $C_1$-$C_4$-alkoxy group or is an aryloxy group or, in particular, is a halogen atom, it is preferred to use the base in at least two-fold excess (i.e. the molar ratio of compound II and the base is preferably at least 1:2, e.g. 1:2 to 1:10 or >1:2 to 1:10, for example 1:2.1 to 1:10 or 1:2.5 to 1:10) in order to cause elimination of this group $R^7$, too, and thus to arrive directly at the aromatic compound I.

If the compound II does not carry such a group $R^7$ or not in said position, the firstly resulting cyclohexadiene compound must be oxidized to give the biphenyl compound I.

Oxidation generally takes place in situ if the dehydrohalogenation reaction is carried out under air atmosphere and/or if the reaction mixture is left at air atmosphere after the completion of the dehydrohalogenation.

Alternatively, air or oxygen can be sparged through the reaction mixture during the dehydrohalogenation reaction and/or after its completion.

In case the dehydrohalogation reaction is carried out under an inert atmosphere, e.g. under nitrogen or argon, for instance because the base used is sensitive to moisture, air or oxygen can be sparged through the reaction mixture after the completion of the dehydrohalogenation reaction or dry air or dry oxygen can be sparged through the reaction mixture during the dehydrohalogenation reaction, optionally in the presence of one of the below-described oxidation catalysts. Alternatively, the resulting reaction mixture may be reacted with one of the below-described oxidizing agents.

If oxidation is carried out by air or oxygen, this may be supported by a suitable oxidation catalyst. Suitable catalysts are for example metals like Fe, Co, Ni, Cu, Ag, V or Mn in form of the metals as such or of their salts, for instance as halides, sulfates, nitrates or acetates, and molybdovanado phosphoric acids.

However, it is preferred to carry out the oxidation without a catalyst.

Alternatively, the cyclohexadiene compound obtained in the elimination step may be reacted with an oxidizing agent (of course oxygen and air are oxidizing agents, too, but in this context, this term denotes compounds different therefrom). Suitable oxidizing agents are for example potassium permanganate, barium manganate, manganese dioxide, selenium dioxide, sodium periodate, lead(IV) acetate, ammonium molybdate, hydrogen peroxide, persulfates, such as oxone, activated carbon, sulphur, quinones, such as benzoquinone, chloroanil and 2,3-dichloro-5,6-dicyan-p-benzoquinoe (DDQ), nitric acid, nitric acid esters, cerium ammonium nitrate, tert-butylnitrite, nitrogen oxides, $K_3[Fe(CN)_6]$ and electrochemical methods. A preferred oxidizing agent is manganese dioxide.

Particularly preferably aromatization is accomplished by carrying out the dehydrohalogenation reaction under air atmosphere and/or by keeping the reaction mixture at air atmosphere after the completion of the dehydrohalogenation; or by sparkling air or oxygen through the reaction mixture during the dehydrohalogenation reaction and/or after its completion; or by oxidizing the product of the dehydrohalogenation reaction with an oxidizing agent, specifically with $MnO_2$.

Reactions using the above oxidizing agents are principally known and are described, for example, in DE-A-102006016462 and the literature cited therein.

The oxidizing agent is preferably used in at least equimolar ratio, which means that compound II and the oxidising agent are used in a molar ration of at least 1:1, preferably of 1:>1, for example 1:1.1 to 1:10 or 1:1.5 to 1:10, and more preferably 1:1.5 to 1:5.

If the oxidation is carried out with an oxidizing agent different from air and oxygen, the oxidizing agent may be added to the reaction mixture after the elimination reaction is completed. The completion of the elimination reaction may be monitored by known means, for instance by determining the amount of eliminated HX or by TLC or NMR.

Alternatively, the elimination product, i.e. the cyclohexadiene compound, may be first isolated, for instance by extractive or distillative methods, and then reacted with the oxidizing agent.

In this case, the oxidation is preferably carried out in a suitable solvent. Suitable solvents are for example aliphatic hydrocarbons, such as pentane, hexane, heptane, octane and petroleum ether, cycloaliphatic hydrocarbons, such as cyclohexane, methylcyclohexane, cyclooctane, decaline and tetraline, chlorinated alkanes, such as dichloromethane, chloroform, tetrachloromethane, dichloroethylene and trichloroethylene, aromatic hydrocarbons, such as benzene, chlorobenzene, dichlorobenzene, nitrobenzene, toluene, nitrotoluene and the xylenes, aliphatic ethers, such as diethylether, dipropylether, dibutylether, methyl-tert-butylether and methyl-isopropylether, esters of aliphatic monocarboxylic acids, such as ethylacetate, propylacetate, isopropylacetate, butylacetate, ethylpropionate and propylpropionate, nitriles, such as acetonitrile, butyronitrile and valeronitrile, $C_1$-$C_4$-alcohols, such as methanol, ethanol, propanol, isopropanol, butanol, sec-butanol, isobutanol and tert-butanol, glycols, such as ethylene glycol and propylene glycol, glycol ethers, such as diethylene glycol and triethylene glycol, monoglycolmomoether, such as ethyleneglycolmonomethylether, $C_3$-$C_5$-ketones, such as acetone, ethylmethylketone and methylisobutylketone, cyclic ethers, such as tetrahydrofuran and dioxane, amides, such as dimethylformamide (DMF) and dimethylacetamide, dimethylsulfoxide, water and mixtures of these solvents.

The solvent is preferably chosen so as to dissolve the reactants, i.e. the cyclohexadiene compound and the oxidizing agent at least partly, e.g. at least 5% by weight of each of the reactants.

If the oxidizing agent differs completely from the cyclohexadiene compound with respect to its solubility, it is also possible to carry out the oxidation in a biphasic system comprising water and a solvent which is essentially immiscible with water. The biphasic system may also comprise a phase transfer catalyst. With respect to suitable and preferred solvents essentially immiscible with water and phase transfer catalyst reference is made to what has been said above in context with the elimination reaction.

In case of the preferably used manganese dioxide, the solvent is preferably selected from the above-mentioned polar solvents, especially from the above-mentioned polar-aprotic solvents such as DMF.

Yet in another alternative, the oxidizing agent may be added from the beginning of the elimination reaction to the reaction mixture. In this case, and also in case the elimination reaction is carried out in the presence of air or oxygen, the oxidative dehydrogenation may be faster than the dehydrohalogenation, thus formally first resulting in a cyclohexadiene which is still substituted by X.

In processes A, B and C of the invention, in the term "if necessary aromatizing the resulting product" the expression "if necessary" refers to the fact that during the elimination step, as already explained above, aromatization can take place in situ without requiring any specific measures to be taken, for instance via in situ elimination of a suitable group $R^7$ or via in situ dehydrogenation induced by air or oxygen or a different oxidation agent which is present from the beginning of the elimination step.

In case an oxidizing agent different from air and oxygen is used, the oxidation reaction is preferably carried out a temperature of from −10 to 200° C. The suitable temperature depends on the oxidation agent chosen and can be determined by the skilled person, for instance by simple preliminary tests.

The formed biphenyl compound I is isolated from the reaction mixture by known means, for example in case an organic solvent has been used, by first removing this, then suspending the residue in water, extracting the aqueous phase with a suitable solvent and removing the solvent from the organic phase, or in case a biphasic solvent system has been used, separating the two phases and removing the solvent from the organic phase. If desired, the thusly isolated biphenyl compound I is then subjected to one or more purification steps, such as extraction, distillation under reduced pressure, melt crystallization, recrystallization or chromatographic methods.

Preferably, the compound of formula II is obtained by reacting a compound of formula III

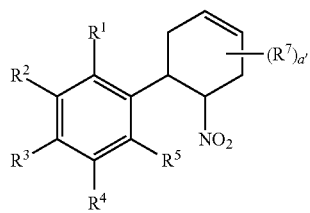

(III)

wherein $R^1$, $R^2$, $R^3$, $R^4$, $R^5$, $R^7$ and a' have one of the above-given general or preferably one of the preferred meanings, with a halogenating agent.

Suitable halogenating agents are for example halogen, such as chlorine, bromine or iodine, N-halogensuccinimides, such as N-chlorosuccinimide, N-bromosuccinimide or N-iodosuccinimide, and 1,3-dibromo-5,5-dimethyl hydantoine.

Preferably, the compound of formula III is reacted with chlorine, bromine, iodine, N-chlorosuccinimide, N-bromosuccinimide, N-iodosuccinimide or 1,3-dibromo-5,5-dimethyl hydantoine, more preferably with chlorine, bromine, N-chlorosuccinimide, N-bromosuccinimide or 1,3-dibromo-5,5-dimethyl hydantoine. Specifically, the compound of formula III is reacted with bromine, N-bromosuccinimide or N-chlorosuccinimide.

The compound of formula III and the halogenating agent are preferably used in a molar ratio of from 1:1 to 1:10, more preferably 1:1 to 1:5, even more preferably from 1:1 to 1:3, in particular from 1:1 to 1:2 and specifically from 1:1.1 to 1:1.5.

Preferably the halogenation of compound III is carried out in the presence of a base, in particular if a halogen is used as halogenating agent. But also if another halogenating agent is used, it is preferred to carry out the reaction in the presence of a base.

Suitable bases are inorganic or organic bases.

Suitable inorganic bases comprise alkali metal hydroxides, such as lithium, sodium or potassium hydroxide, earth alkaline metal hydroxides, such as magnesium or calcium hydroxide, alkali metal carbonates, such as lithium, sodium or potassium carbonate, and earth alkaline metal carbonates, such as magnesium or calcium carbonate. Preferred inorganic bases are alkali metal hydroxides, such as lithium, sodium or potassium hydroxide.

Suitable organic bases comprise alkali metal $C_1$-$C_4$-alkoxides, such as sodium methoxide, potassium methoxide, sodium ethoxide, potassium ethoxide, sodium propoxide, potassium propoxide, sodium isopropoxide, potassium isopropoxide, sodium butoxide, potassium butoxide, sodium tert-butoxide and potassium tert-butoxide, organic aliphatic amines, such as methylamine, dimethylamine, trimethylamine, ethylamine, diethylamine, triethylamine, propylamine, dipropylamine, tripropylamine, diisopropylethylamine, butylamine, dibutylamine, tributylamine, ethanolamine, diethanolamine and triethanolamine, cyclic amidines, such as 1,8-diazabicyclo[5.4.0]undec-7-en (DBU) and 1,5-diazabicyclo[4.3.0]non-5-ene (DBN), and basic, saturated, partially unsaturated or aromatic heteromono- or bicyclic rings containing at least one nitrogen ring atom and 5 to 10 ring members, such as pyrrolidine, pyrazolidine, imidazolidine, oxazolidine, isoxazolidine, thiazolidine, isothiazolidine; piperidine, piperazine, pyridine, lutidine, picoline, 1,4-diazabicyclo[2.2.2]octane (DABCO) and the like. Preferred organic bases are alkali metal $C_1$-$C_4$-alkoxides, such as sodium methoxide, potassium methoxide, sodium ethoxide, potassium ethoxide, sodium propoxide, potassium propoxide, sodium isopropoxide, potassium isopropoxide, sodium butoxide, potassium butoxide, sodium tert-butoxide and potassium tert-butoxide. More preferred are sodium tert-butoxide and potassium tert-butoxide and in particular potassium tert-butoxide.

Preference is given to the use of inorganic bases. Preferred inorganic bases are alkali metal hydroxides, such as lithium, sodium or potassium hydroxide. More preferred inorganic bases are sodium hydroxide and, in particular, potassium hydroxide.

The compound of formula III and the base are preferably used in a molar ratio of from 1:1 to 1:10, more preferably 1:1 to 1:5, even more preferably from 1:1 to 1:3, in particular from 1:1 to 1:2 and specifically from 1:1 to 1:1.5.

The halogenation reaction is generally carried out in a suitable solvent. Suitable solvents are chosen so as to dissolve at least partially the reactants, i.e. compound III, the halogenating agent and if appropriate the base. Of course the solvent is not to negatively interfere with the halogenation reaction.

Suitable solvents are for example $C_1$-$C_4$-alcohols, such as methanol, ethanol, propanol, isopropanol, butanol, sec-butanol, isobutanol and tert-butanol, glycols, such as ethylene glycol and propylene glycol, glycol ethers, such as diethylene glycol and triethylene glycol, $C_3$-$C_4$-ketones, such as acetone and ethylmethylketone, cyclic ethers, such as tetrahydrofuran and dioxane, amides, such as dimethylformamide (DMF) and dimethylacetamide, dimethylsulfoxide, aliphatic hydrocarbons, such as pentane, hexane, heptane, octane and petroleum ether, cycloaliphatic hydrocarbons, such as cyclohexane and cyclooctane, chlorinated alkanes, such as dichloromethane, chloroform, tetrachloromethane, dichloroethylene and trichloroethylene, aromatic hydrocarbons, such as benzene, toluene and the xylenes, aliphatic ethers, such as diethylether, dipropylether, dibutylether, methyl-tert-butylether and methyl-isopropylether, and esters of aliphatic monocarboxylic acids, such as ethylacetate, propylacetate, ethylpropionate and propylpropionate, and mixtures thereof.

In case an inorganic base is used, preference is given in this reaction step to the use of a polar organic solvent, such as $C_1$-$C_4$-alcohols, for example methanol, ethanol, propanol, isopropanol, butanol, sec-butanol, isobutanol or tert-butanol, glycols, for example ethylene glycol or propylene glycol, glycol ethers, for example diethylene glycol or triethylene glycol, $C_3$-$C_4$-ketones, for example acetone or ethylmethylketone, cyclic ethers, for example tetrahydrofuran or dioxane, amides, for example dimethylformamide (DMF) or dimethylacetamide, and dimethylsulfoxide; further dichloromethane, chloroform, ethylacetate, toluene or mixtures thereof.

Preferably, a protic solvent, such as $C_1$-$C_4$-alcohols, for example methanol, ethanol, propanol, isopropanol, butanol, sec-butanol, isobutanol or tert-butanol, glycols, for example ethylene glycol or propylene glycol, glycol ethers, for example diethylene glycol or triethylene glycol, $C_3$-$C_4$-ketones, for example acetone or ethylmethylketone, cyclic ethers, for example tetrahydrofuran or dioxane, amides, for example dimethylformamide (DMF) or dimethylacetamide, and dimethylsulfoxide, is used.

More preferably, a polar protic solvent is used. Suitable polar protic solvents comprise $C_1$-$C_4$-alcohols, such as methanol, ethanol, propanol, isopropanol, butanol, sec-butanol, isobutanol and tert-butanol, glycols, such as ethylene glycol and propylene glycol, and glycol ethers, such as diethylene glycol and triethylene glycol. Preference is given to the above-mentioned alcohols, $C_1$-$C_3$-alcohols (i.e. methanol, ethanol, propanol and isopropanol) being more preferred.

The polar protic solvent may also comprise up to 30% by weight, preferably up to 20% by weight, more preferably up to 15% by weight, of a polar aprotic and/or an apolar solvent. Suitable apolar solvents are those mentioned above as "essentially immiscible with water". Preferred apolar solvents are the above-mentioned aromatic hydrocarbons, especially toluene, the above-mentioned chloroalkanes, especially dichloromethane, and the above-mentioned esters, especially ethylacetate.

In case an organic base is used, all of the above-mentioned suitable solvents and mixtures thereof can be used.

The halogenation reaction is generally carried out at from 0° C. to the boiling point of the reaction mixture, preferably at from 0 to 40° C. and more preferably at from 10 to 30° C.

In case the halogenation is carried out in the presence of a base, preferably compound III is first mixed with the base and subsequently, the halogenating agent is added. Alternatively, compound III can first be mixed with the halogenating agent and the base then be added to this reaction mixture. However, the first variant is preferred.

Compound II can be isolated from the reaction mixture and purified by known methods. For instance, the solvent can be removed, e.g. by distillation, preferably under reduced pressure, and the residue can be suspended in an aqueous solution and extracted with a suitable organic solvent which is then removed from the extract, or the residue can be subjected to a chromatographic purification step.

The compound of formula III is preferably obtained by reaction (Diels-Alder reaction) of a compound of formula IV

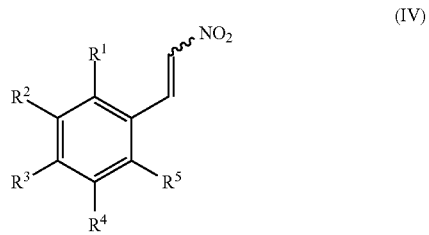

wherein $R^1$, $R^2$, $R^3$, $R^4$ and $R^5$ have one of the above-given general or preferably one of the preferred meanings, with butadiene or a butadiene derivative.

Suitable butadiene derivatives are sulfolene and a compound of formula IX

where $R^7$ is as defined above and b is 1 or 2.

In compounds IX in which b is 2, the two substituents $R^7$ are not bound to the same carbon atom.

Preferably, $R^7$ is selected from $C_1$-$C_4$-alkyl, $OR^8$, amino, $C_1$-$C_4$-alkylamino and di-($C_1$-$C_4$-alkyl)-amino. More preferably, $R^7$ is selected from $C_1$-$C_4$-alkyl, amino, methylamino, dimethylamino and a group $OR^8$; even more preferably from $C_1$-$C_4$-alkyl, amino, methylamino, dimethylamino and a group $OR^8$, where $R^8$ is preferably selected from $C_1$-$C_4$-alkyl, trimethylsilyl and tert-butyldimethylsilyl (i.e. the group $OR^8$ is preferably selected from $C_1$-$C_4$-alkoxy, trimethylsilyloxy and tert-butyldimethylsilyloxy), and particularly preferably from methyl, dimethylamino and a group $OR^8$, where $R^8$ is preferably selected from $C_1$-$C_4$-alkyl, preferably methyl or ethyl, trimethylsilyl and tert-butyldimethylsilyl (i.e. the group $OR^8$ is preferably selected from $C_1$-$C_4$-alkoxy, preferably methoxy or ethoxy, trimethylsilyloxy and tert-butyldimethylsilyloxy). In particular, $R^7$ is methyl, methoxy or ethoxy and is specifically methyl or methoxy.

If the substituent(s) $R^7$ is/are bound in the 1-position or in the 1,4-positions, they are preferably bound trans so as not to interfere negatively with the cycloaddition reaction.

As indicated in the above formula, the butadiene derivative is preferably in the cisoid conformation or can readily take the cisoid conformation in the course of the cycloaddition reaction.

Preferably, the butadiene derivative is selected from sulfolene and a compound IX wherein $R^7$ is selected from $C_1$-$C_4$-alkyl, $C_1$-$C_4$-alkoxy, amino, methylamino, dimethylamino, trimethylsilyloxy and tert-butyldimethylsilyloxy, more preferably from methyl, methoxy, ethoxy, dimethylamino, trimethylsilyloxy and tert-butyldimethylsilyloxy, in particular from methyl, methoxy or ethoxy and specifically from methyl or methoxy. More preferably, the butadiene derivative is selected from sulfolene, isoprene, piperylene, preferably trans-piperylene, 2,3-dimethyl-1,3-butadiene, 1-methoxy-1,3-butadiene, preferably trans-1-methoxy-1,3-butadiene, 2-methoxy-1,3-butadiene, 1-ethoxy-1,3-butadiene, preferably trans-1-ethoxy-1,3-butadiene, 2-ethoxy-1,3-butadiene, 2,3-dimethoxy-1,3-butadiene, 1-dimethylamino-1,3-butadiene, preferably trans-1-dimethylamino-1,3-butadiene, 1-dimethylamino-3-trimethylsiloxy-1,3-butadiene, preferably trans-1-dimethylamino-3-trimethylsiloxy-1,3-butadiene, and 1-dimethylamino-3-tert-butyldimethylsiloxy-1,3-butadiene, preferably trans-1-dimethylamino-3-tert-butyldimethylsiloxy-1,3-butadiene.

Even more preferably, the butadiene derivative is selected from sulfolene, isoprene, piperylene, preferably trans-piperylene, 2,3-dimethyl-1,3-butadiene, 1-methoxy-1,3-butadiene, preferably trans-1-methoxy-1,3-butadiene, 1-ethoxy-1,3-butadiene, preferably trans-1-ethoxy-1,3-butadiene, and 2,3-dimethoxy-1,3-butadiene and in particular from isoprene, piperylene, preferably trans-piperylene, 2,3-dimethyl-1,3-butadiene, 1-methoxy-1,3-butadiene, preferably trans-1-methoxy-1,3-butadiene, 1-ethoxy-1,3-butadiene, preferably trans-1-ethoxy-1,3-butadiene, and 2,3-dimethoxy-1,3-butadiene. Specifically, the butadiene derivative is selected from sulfolene, isoprene, piperylene, preferably trans-piperylene, and 1-methoxy-1,3-butadiene, preferably trans-1-methoxy-1,3-butadiene.

However, it is preferred to react compound IV with butadiene and not with a butadiene derivative.

The Diels-Alder reaction of compound IV and butadiene or the butadiene derivative can be carried out according to known methods, for example as described in M. B. Neher et al., J. Org. Chem. 1961, 26, 5220, E. MacDonald et al., J. Chem. Soc. Perkin Trans. (7), 1979, 1893, W. C. Wildman et al., J. Am. Chem. Soc. 1953, 75(8), 1912-1915 or W. C. Wildman et al., J. Org. Chem. 1952, 17(4), 581-594 and in the literature cited therein.

The compound of formula IV and butadiene are preferably reacted in a molar ratio of from 1:1 to 1:10, more preferably from 1:1 to 1:5 and in particular from 1:1 to 1:3.

The compound of formula IV and the butadiene derivative are preferably reacted in a molar ratio of from 1:1 to 1:5, more preferably from 1:1 to 1:3 and in particular from 1:1 to 1:2.

The Diels-Alder reaction of the compound IV with butadiene or sulfolene is preferably carried out at elevated temperatures, preferably at from 80° C. to 250° C., more preferably from 100° C. to 250° C. and in particular at from 100° C. to 200° C.

In case a butadiene derivative of formula IX is used, the reaction can also be carried out at lower temperatures, for example at from 20° C. to 250° C. or preferably at from 20° C. to 200° C. or more preferably at from 20° C. to 150° C. or even more preferably at from 20° C. to 100° C., depending on the electron-donating effect of the group $R^7$. For instance, if 1-dimethylamino-3-trimethylsiloxy-1,3-butadiene or 1-dimethylamino-3-tert-butyldimethylsiloxy-1,3-butadiene is used, the reaction temperature can be as low as room temperature. However, the reaction rate is of course increased with higher temperatures, and thus also in case of compounds IX it is preferred to use elevated temperatures, such as from 40 to 200° C. or preferably from 50 to 150° C. or from 80 to 120° C.

The Diels-Alder reaction of compound IV and butadiene or the butadiene derivative is carried out at a pressure of preferably from 1 bar to 250 bar, e.g. of from 1.1 to 250 or from 1.5 to 250 or from 2 to 250 bar or from 10 to 250 bar; more preferably from 1.5 to 200 bar, e.g. of from 1.1 to 200 or from 1.5 to 200 or from 2 to 200 bar or from 10 to 200 bar; even more preferably from 1.5 to 150 bar, e.g. of from 1.1 to 150 or from 1.5 to 150 or from 2 to 150 bar or from 10 to 150 bar; in particular from 1 to 10 bar, e.g. of from 1.1 to 10 or from 1.5 to 10 or from 2 to 10 bar; and specifically from 2 to 8 bar.

Especially in case butadiene, which is gaseous under ambient conditions, is used, the reaction is preferably carried out under positive pressure. Preferably, the pressure ranges from 1.1 bar to 250 bar, more preferably from 1.5 to 200 bar, even more preferably from 1.5 to 150 bar and in particular from 2 to 150 bar. In the context of the present invention, "positive pressure" means a pressure of >1 bar. The positive pressure can be generated by butadiene and/or by an inert gas, such as nitrogen or argon. Preferably, the positive pressure is at least partially generated by butadiene, if this is used as reactant. In case a butadiene derivative is used, positive pressure is generally generated by an inert gas.

If a butadiene derivative is used, the reaction can also be carried out under normal pressure.

The reaction is preferably carried out in the presence of a polymerization inhibitor, which is especially preferred in case butadiene is used. Suitable inhibitors comprise, for example, hydroquinone, 4-methoxyphenol, tert-butylhydroquinone, benzoquinone, sterically hindered phenols, such as 2,6-di-(tert-butyl)-para-cresol (BHT), 2-(tert-butyl)-para-cresol or butylhydroxyanisol (BHA), tert-butylcatechol, sterically hindered amines, such as 2,2,6,6-tetramethylpiperidin-1-oxyl or 4-hydroxy-2,2,6,6-tetramethylpiperidin-1-oxyl, p-phenylenediamine or phenothiazine. Preferably, one of the above-mentioned hydroquinones or phenols is used. Specifically, the reaction is carried out in the presence of hydroquinone.

The Diels-Alder reaction is preferably carried out in a suitable solvent. Suitable solvents are those in which the reactants are soluble and have a boiling point high enough for being liquid under the given reaction conditions. In case the butadiene derivative used is liquid, it can also serve as a solvent and thus the Diels-Alder reaction can be carried out in substance. However, the presence of a solvent different from the butadiene derivative is preferred.

Suitable solvents are for example $C_1$-$C_4$-alcohols, such as methanol, ethanol, propanol, isopropanol, butanol, sec-butanol, isobutanol and tert-butanol, glycols, such as ethylene glycol and propylene glycol, glycol ethers, such as diethylene glycol and triethylene glycol, $C_3$-$C_4$-ketones, such as acetone and ethylmethylketone, cyclic ethers, such as tetrahydrofuran and dioxane, amides, such as dimethylformamide (DMF) and dimethylacetamide, dimethylsulfoxide, aliphatic hydrocarbons, such as pentane, hexane, heptane, octane and petroleum ether, cycloaliphatic hydrocarbons, such as cyclohexane and cyclooctane, chlorinated alkanes, such as dichloromethane, chloroform, tetrachloromethane, dichloroethylene and trichloroethylene, aromatic hydrocarbons, such as benzene, toluene and the xylenes, aliphatic ethers, such as diethylether, dipropylether, dibutylether, methyl-tert-butylether and methyl-isopropylether, and esters of aliphatic monocarboxylic acids, such as ethylacetate, propylacetate, ethylpropionate and propylpropionate, and mixtures thereof. Preferred solvents are the above-mentioned aromatic hydrocarbons, optionally as a mixture with one of the above-mentioned chlorinated alkanes, toluene, optionally as a mixture with dichloromethane or chloroform, being particularly preferred.

The Diels-Alder reaction, if carried out under positive pressure, is suitably carried out in a reactor which can be pressurized, such as a pressure vessel, an autoclave or a pressurized reactor.

After completion of the reaction, the compound III is generally isolated from the reaction mixture by usual measures, for example by at least partly removing the solvent, for example by distillation, preferably under reduced pressure, and removing excess butadiene or butadiene derivative.

Excess butadiene can be removed by distillation and exhausts yet when the reaction vessel is depressurized.

Preferably, the compound of formula IV is prepared by reacting a compound of formula V

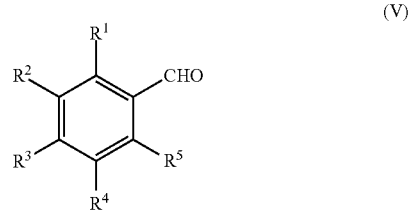

wherein $R^1$, $R^2$, $R^3$, $R^4$ and $R^5$ have one of the above-given general or preferably one of the preferred meanings, with nitromethane.

In this reaction (which can be called a nitro-aldol reaction), compound V and nitromethane are preferably reacted in a molar ratio of from 1:1 to 1:15, more preferably from 1:1 to 1:10, even more preferably from 1:1 to 1:7, in particular from 1:1 to 1:5 and specifically from 1:1 to 1:2. Very particularly, the compound V and nitromethane are used in a molar ratio of from 1:1 to 1:1.5 and even more particularly in essentially equimolar amounts. "Essentially equimolar" means that this is to be understood to include error limits, for example due to measuring inaccuracy.

The reaction is preferably carried out in the presence of a base. In this case, the reaction is called a Henry reaction.

In this case, compound V and nitromethane are preferably reacted in a molar ratio of from 1:1 to 1:5, more preferably from 1:1 to 1:2, even more preferably from 1:1 to 1:1.5, in particular from 1:1 to 1:1.1 and specifically in essentially equimolar amounts. "Essentially equimolar" means that this is to be understood to include error limits, for example due to measuring inaccuracy.

Suitable bases are those mentioned above for the elimination step. Preferably, organic bases are used. Among these, alkali metal $C_1$-$C_4$-alkoxides and alkali metal hydroxides are preferred, the alkali metal $C_1$-$C_4$-alkoxides being more preferred.

The compound V and the base are preferably used in a molar ratio of from 1:1 to 1:10, more preferably from 1:1 to 1:5 and in particular from 1:1 to 1:2. The base may also be used in catalytic, i.e. substoichiometric amounts, however the use of at least stoichiometric amounts is preferred.

The base not only catalyzes the first step of the aldol-analogous formation of a β-nitroalkoholate, but also the elimination of water in a subsequent step by which compound IV is produced. However, the elimination is more effectively catalyzed by acids and thus it is preferred to acidify the reaction mixture after the completion of the aldolization (i.e. the formation of the (β-nitroalkoholate) in order to obtain an essentially complete elimination of water from the β-nitroalkoholate.

Suitable acids are both inorganic (mineral) acids and organic acids. Suitable inorganic acids are for example hydrochloric acid, hydrobromic acid, sulphuric acid, nitric acid, phosphoric acid and ammonium salts, such as ammonium-chloride. Suitable organic acids are for example aliphatic monocarboxylic acids with preferably 1 to 6 carbon atoms, such as fumaric acid, acetic acid, trifluoroacetic acid, propionic acid, butyric acid, valeric acid, isovaleric acid and caproic acid, aromatic carboxylic acids, such as benzoic acid, and sulfonic acids, such as methanesulfonic acid, trifluoromethanesulfonic acid or toluenesulfonic acid.

Preference is made to organic acids. Preferred organic acids are aliphatic monocarboxylic acids with 1 to 4 carbon atoms, such as fumaric acid, acetic acid, trifluoroacetic acid, propionic acid and butyric acid. More preferably, acetic acid is used, in particular in the form of anhydrous acetic acid or acetic anhydride.

The acid is used in such an amount that the base is neutralized and that the molar ratio of the acid theoretically left over after the neutralization and compound V is from 1:1 to 10:1, more preferably from 1:1 to 5:1. The required quantity depends on the pKA of the acid used and is the smaller the stronger the acidity.

Alternatively, the reaction can also be carried out entirely in the presence of an acid.

In this case, compound V and nitromethane are preferably reacted in a molar ratio of from 1:1 to 1:15, more preferably from 1:1.5 to 1:10, even more preferably from 1:1.5 to 1:7, in particular from 1:2 to 1:7 and specifically from 1:3 to 1:7, for example from 1.4 to 1.6.

Suitable acids are those mentioned above. In this case, too, preference is made to organic acids. Preferred organic acids are aliphatic monocarboxylic acids with 1 to 4 carbon atoms, such as fumaric acid, acetic acid, trifluoroacetic acid, propionic acid and butyric acid. More preferably, acetic acid is used, in particular in the form of anhydrous acetic acid or acetic anhydride.

The suitable quantity of the acid depends inter alia on its pKA. In general a stronger acid (i.e. an acid with a low pKA) is used in lower quantities than a weaker acid.

Preferably, compound V and the acid are used in a molar ratio of from 1:1 to 1:20, more preferably from 1:1 to 1:10, even more preferably from 1:1 to 1:5 and in particular from 1:1 to 1:2.

However, it is preferred to carry out the reaction in the presence of a base.

The reaction of compound V and nitromethane is preferably carried out in a suitable solvent. Suitable solvents are chosen so as to dissolve at least partially the reactants, i.e. compound V, nitromethane and if appropriate the base or the acid. Of course the solvent is not to negatively interfere with the nitro-aldol reaction.

Suitable solvents are for example $C_1$-$C_4$-alcohols, such as methanol, ethanol, propanol, isopropanol, butanol, sec-butanol, isobutanol and tert-butanol, glycols, such as ethylene glycol and propylene glycol, glycol ethers, such as diethylene glycol and triethylene glycol, $C_3$-$C_4$-ketones, such as acetone and ethylmethylketone, cyclic ethers, such as tetrahydrofuran and dioxane, amides, such as dimethylformamide (DMF) and dimethylacetamide, dimethylsulfoxide, aliphatic hydrocarbons, such as pentane, hexane, heptane, octane and petroleum ether, cycloaliphatic hydrocarbons, such as cyclohexane and cyclooctane, chlorinated alkanes, such as dichloromethane, chloroform, tetrachloromethane, dichloroethylene and trichloroethylene, aromatic hydrocarbons, such as benzene, toluene and the xylenes, aliphatic ethers, such as diethylether, dipropylether, dibutylether, methyl-tert-butylether and methyl-isopropylether, and esters of aliphatic monocarboxylic acids, such as ethylacetate, propylacetate, ethylpropionate and propylpropionate, and mixtures thereof. Preference is given to the above aromatic hydrocarbons, in particular toluene, the above chloroalkanes, in particular dichloromethane, the above alcohols, in particular $C_1$-$C_3$-alcohols, such as methanol, ethanol, propanol or isopropanol, and mixtures thereof.

The reaction can for example be carried out by mixing compound V and nitromethane in a solvent and adding a base to this mixture. It is also possible to add compound V to a mixture of the base and nitromethane or to add nitromethane to a mixture of compound V and the base or to introduce all components simultaneously into the reaction vessel, however the first variant is preferred. This step is preferably carried out at from −20 to 20° C., more preferably from −10 to 15° C., even more preferably from 0 to 10° C. and specifically from 0 to 5° C. After completion of the aldolization, the mixture is preferably neutralized with an acid and then acidified for eliminating water from the nitro aldol. This elimination is preferably carried out at from 20° C. to the boiling point of the reaction mixture, more preferably from 30 to 80° C. and in particular from 40 to 60° C.

Workup and isolation can be carried out by known methods, for example by extractive and/or chromatographic methods and/or by crystallization.

The compounds of formula V are either commercially available or can be prepared by principally known methods. For instance the bromide of formula IX

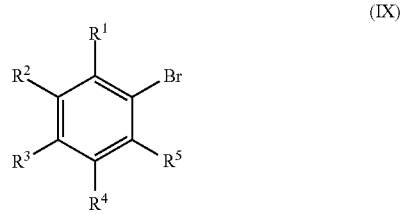

(IX)

can be metallated with, for example, n-butyllithium (n-BuLi), methyllithium (MeLi) or phenyllithium (PhLi) and then reacted with a formyl source, such as methylformiate, ethylformiate and the like.

By the above-described method, compounds of formula I can be obtained in a high yield, using low-cost reactants and avoiding the use of expensive metal catalysts, especially of expensive transition metal catalysts.

The compounds I can be further reacted to compounds of formula VI by reducing the nitro group. Reduction may be carried out with hydrogen in the presence of a hydrogenation catalyst or with other reduction agents, such as $SnCl_2/HCl$, Fe/HCl or $Fe/NH_4Cl$.

Reduction can be carried out according to known methods of converting aromatic nitro compounds into the corresponding aromatic amino compounds, such as described, for example, in R. J. Rahaim, R. E. Maleczka (Jr.), Org. Lett., 2005, 7, 5087-5090, G. S. Vanier, Synlett, 2007, 131-135, S. Chandrasekhar, S. Y. Prakash, C. L. Rao, J. Org. Chem., 2006, 71, 2196-2199, H. Berthold, T. Schotten, H. Hönig, Synthesis, 2002, 1607-1610, and C. Yu, B. Liu, L. Hu, J. Org. Chem., 2001, 66, 919-924.

The hydrogenation catalysts may generally be all prior art catalysts which catalyze the reduction of a nitro group to an amino group without hydrogenating the phenyl ring to which this is bound. The catalysts may be used either in heterogeneous phase or as homogeneous catalysts. The hydrogenation catalysts preferably comprise at least one metal of group VIII.

Particularly suitable metals of group VIII are selected from ruthenium, cobalt, rhodium, nickel, palladium und platinum and especially from palladium und platinum.

The metals may also be used in the form of mixtures. Moreover, the catalysts may comprise, in addition to the metals of group VIII, also small amounts of further metals, for example metals of group VIIa, in particular rhenium, or metals of group Ib, i.e. copper, silver or gold.

When a heterogeneous catalyst is used, it is suitably present in finely divided form. The finely divided form is achieved, for example, as follows:
a) Black catalyst: shortly before use as a catalyst, the metal is deposited reductively from the solution of one of its salts.
b) Adams catalyst: the metal oxides, in particular the oxides of platinum and palladium, are reduced in situ by the hydrogen used for the hydrogenation.
c) Skeletal or Raney catalyst: the catalyst is prepared as a "metal sponge" from a binary alloy of the metal (in particular nickel or cobalt) with aluminum or silicon by leaching out one partner with acid or alkali. Residues of the original alloy partner often act synergistically.
d) Supported catalyst: black catalysts can also be precipitated on the surface of a support substance. Suitable supports and support materials are described below.

Such heterogeneous catalysts are described in general form, for example, in Organikum, 17th edition, VEB Deutscher Verlag der Wissenschaften, Berlin, 1988, p. 288.

Depending on the configuration of the hydrogenation process, the support material can take various forms. When the hydrogenation is carried out in liquid phase mode, the support material is generally used in the form of a fine powder. On the other hand, when the catalyst is used in the form of a fixed bed catalyst, the support material used is, for example, shaped bodies. Such shaped bodies may be present in the form of spheres, tablets, cylinders, hollow cylinders, Raschig rings, extrudates, saddles, stars, spirals, etc., having a size (length of longest dimension) of from about 1 to 30 mm. Moreover, the supports may be present in the form of monoliths, as described, for example, in DE-A-19642770. In addition, the supports may be used in the form of wires, sheets, grids, meshes, fabrics and the like.

The supports may consist of metallic or nonmetallic, porous or nonporous material.

Suitable metallic materials are, for example, highly alloyed stainless steels. Suitable nonmetallic materials are, for example, mineral materials, for example natural and synthetic minerals, glasses or ceramics, plastics, for example synthetic or natural polymers, or a combination of the two.

Preferred support materials are carbon, in particular activated carbon, silicon dioxide, in particular amorphous silicon dioxide, alumina, and also the sulfates and carbonates of the alkaline earth metals, calcium carbonate, calcium sulfate, magnesium carbonate, magnesium sulfate, barium carbonate and barium sulfate.

The catalyst may be applied to the support by customary processes, for example by impregnating, wetting or spraying the support with a solution which comprises the catalyst or a suitable precursor thereof.

Suitable supports and processes for applying the catalyst thereto are described, for example, in DE-A-10128242, which is hereby fully incorporated by reference.

It is also possible to use homogeneous hydrogenation catalysts in the process according to the invention. However, disadvantages of use of homogeneous catalysts are their preparation costs and also the fact that they generally cannot be regenerated.

Therefore, preference is given to using heterogeneous hydrogenation catalysts in the process according to the invention.

The heterogeneous catalysts used in the process according to the invention more preferably comprise at least one metal of transition group VIII which is selected from ruthenium, nickel, cobalt, palladium and platinum, and which has, if appropriate, been doped with a further transition metal, in particular with one of transition group VIIa, Ib or IIb and in particular with copper.

The metal is more preferably used in supported form or as metal sponge. Examples of supported catalysts are in particular palladium, platinum, nickel or ruthenium on carbon, in particular activated carbon, silicon dioxide, in particular on amorphous silicon dioxide, barium carbonate, calcium carbonate, magnesium carbonate or alumina, and the supports may be present in the above-described shapes. Preferred support shapes are the above-described shaped bodies.

The metallic catalysts may also be used in the form of their oxides, in particular palladium oxide, platinum oxide or nickel oxide, which are then reduced under the hydrogenation conditions to the corresponding metals.

The amount of catalyst to be used depends on factors including the particular catalytically active metal and its use form, and may be determined in the individual case by those skilled in the art. The amount of catalyst specified relates to the amount of active metal, i.e. to the catalytically active component of the catalyst. When noble metal catalysts are used which comprise, for example, platinum or palladium, values smaller by a factor of 10 apply as compared to other group VIII metals.

The hydrogenation is effected at a temperature of preferably from 20 to 250° C., more preferably from 30 to 200° C. and in particular from 50 to 200° C., e.g. from 70 to 150° C. or from 80 to 120° C.

The reaction pressure of the hydrogenation reaction is preferably in the range from 1 to 300 bar, e.g. from 1.5 to 300 bar or 2 to 300 bar; more preferably from 1 to 100 bar, e.g. from 1.5 to 100 bar or 2 to 100 bar; and in particular from 1 to 10 bar, e.g. from 1.5 to 10 bar or 2 to 10 bar.

Both reaction pressure and reaction temperature depend upon factors including the activity and amount of the hydrogenation catalyst used and may be determined in the individual case by those skilled in the art.

In a specific embodiment, the reduction is carried out by using Pd, for example as a Pd(II) salt, in the presence of polymethylhydrosiloxane and KF. The reaction can be carried out under mild conditions, such as room temperature, in analogy to the method described by R. J. Rahaim and R. E. Maleczka (Jr.) in Org. Lett., 2005, 7, 5087-5090.

In another specific embodiment, the reduction is carried out by using Pd on activated carbon and microwave activation in analogy to the method described by G. S. Vanier in Synlett, 2007, 131-135.

In another specific embodiment, the reduction is carried out by using the Adams catalyst $PtO_2$ and a polyethyleneglycol as solvent in analogy to the method described by S. Chandrasekhar, S. Y. Prakash and C. L. Rao in J. Org. Chem., 2006, 71, 2196-2199.

In another specific embodiment, the reduction is carried out by using Pd on activated carbon, a fumarate as hydrogen source and an ionic liquid as solvent in analogy to the method described by H. Berthold, T. Schotten and H. Honig in Synthesis, 2002, 1607-1610.

In another specific embodiment, the reduction is carried out by using Pt on activated carbon.

In another specific embodiment, the reduction is carried out by using a samarium and 1,1'-dialkyl-4,4'-bipyridinium salt as an electron transfer agent in analogy to the method described by C. Yu, B. Liu and L. Hu in J. Org. Chem., 2001, 66, 919-924.

In another specific embodiment, the reduction is carried out by reacting compound I with $SnCl_2$ and concentrated HCl agent in analogy to the method described by L. Caron, L.-C. Campeau and K. Fagnou in Org. Lett. 2008.

In another specific embodiment, the reduction is carried out by reacting compound I with Fe in the presence of $NH_4Cl$ in analogy to the method described by F.-X. Felpin, Adv. Synth. Catal. 2009, 351, 649-655.

The compound VI may then be subjected to an N-acylation with the acyl compound VIII to obtain a compound of formula VII.

In the compounds of the formulae VII and VIII, Y is preferably 5- or 6-membered hetaryl having 1, 2 or 3 nitrogen atoms as ring members, where the hetaryl radical optionally bears 1, 2 or 3 substituents which are preferably selected from halogen, $C_1$-$C_4$-alkyl and $C_1$-$C_4$-haloalkyl. The 5- or 6-membered hetaryl radical Y preferably bears 1 or 2 substituents which are preferably selected from halogen, $C_1$-$C_4$-alkyl and $C_1$-$C_4$-haloalkyl.

The 5- or 6-membered hetaryl radicals with 1, 2 or 3 nitrogen atoms as ring members is, for example, pyrrolyl such as 1-, 2- or 3-pyrrolyl, pyrazolyl such as 1-, 3-, 4- or 5-(1H)-pyrazolyl, imidazolyl such as 1-, 3-, 4- or 5-(1H)-imidazolyl, triazolyl such as 1-, 4- or 5-[1,2,3]-(1H)-triazolyl, 2- or 4-[1,2,3]-(2H)-triazolyl, pyridyl such as 2-, 3- or 4-pyridyl, pyrazinyl such as 2-pyrazinyl, pyrimidinyl such as 2-, 4- or 5-pyrimidinyl, pyridazinyl such as 3- or 4-pyridazinyl, or triazinyl such as 2-[1,3,5]-triazinyl. The 5- or 6-membered hetaryl radical with 1, 2 or 3 nitrogen atoms as ring members is preferably pyrazolyl such as 1-, 3-, 4- or 5-(1H)-pyrazolyl, or pyridyl such as 2-, 3- or 4-pyridyl, and especially pyrazol-4-yl or pyridin-3-yl.

Y is especially 2-chloropyrid-3-yl, 1-methyl-3-(trifluoromethyl)pyrazol-4-yl, 1-methyl-3-(difluoromethyl)pyrazol-4-yl or 1,3-dimethyl-5-fluoropyrazol-4-yl.

For the inventive N-acylation of an aminobiphenyl of the formula VI, the reagent of the formula (VIII) used is generally a carboxylic acid or a derivative of a carboxylic acid capable of amide formation, for instance an acid halide, acid anhydride or ester. Accordingly, the leaving group W is typically hydroxyl, halide, especially chloride or bromide, an —$OR^7$ radical or an —O—CO—$R^8$ radical.

When the compound VIII is used in the form of the carboxylic acid (Y—COOH; W=OH), the reaction can be performed in the presence of a coupling reagent. Suitable coupling reagents (activators) are known to those skilled in the art and are, for example, selected from carbodiimides such as DCC (dicyclohexylcarbodiimide) and DCI (diisopropylcarbodiimide), benzotriazole derivatives such as HBTU ((O-benzotriazol-1-yl)-N,N',N'-tetramethyluronium hexafluorophosphate) and HCTU (1H-benzotriazolium 1-[bis (dimethylamino)methylene]-5-chlorotetrafluoroborate), and phosphonium activators such as BOP ((benzotriazol-1-yloxy) tris(dimethylamino)phosphonium hexafluorophosphate), Py-BOP ((benzotriazol-1-yloxy) tripyrrolidinephosphonium hexafluorophosphate) and Py-BrOP (bromotripyrrolidinephosphonium hexafluorophosphate). In general, the activator is used in excess. The benzotriazole and phosphonium coupling reagents are generally used in a basic medium.

Suitable derivatives of the carboxylic acid Y—COOH are all derivatives which can react with the 2-aminobiphenyl VI to give the amide VII, for example esters Y—C(O)—$OR^7$ (W=$OR^7$), acid halides Y—C(O)X in which X is a halogen atom (W=halogen), or acid anhydrides Y—CO—O—OC—$R^8$ (W=—O—CO—$R^8$).

The acid anhydride Y—CO—O—OC—$R^8$ is either a symmetric anhydride Y—CO—O—OC—Y ($R^8$=Y) or an asymmetric anhydride in which —O—OC—$R^8$ is a group which can be displaced easily by the 2-aminobiphenyl (VI) used in the reaction. Suitable acid derivatives with which the carboxylic acid Y—COOH can form suitable mixed anhydrides are, for example, the esters of chloroformic acid, for example isopropyl chloroformate and isobutyl chloroformate, or of chloroacetic acid.

Suitable esters Y—COOR$^7$ derive preferably from $C_1$-$C_4$-alkanols R$^7$OH in which R$^7$ is $C_1$-$C_4$-alkyl, such as methanol, ethanol, propanol, isopropanol, n-butanol, butan-2-ol, isobutanol and tert-butanol, preference being given to the methyl and ethyl esters (R$^7$=methyl or ethyl). Suitable esters may also derive from $C_2$-$C_6$-polyols such as glycol, glycerol, trimethylolpropane, erythritol, pentaerythritol and sorbitol, preference being given to the glyceryl ester. When polyol esters are used, it is possible to use mixed esters, i.e. esters with different R$^7$ radicals.

Alternatively, the ester Y—COOR$^7$ is a so-called active ester, which is obtained in a formal sense by the reaction of the acid Y—COOH with an active ester-forming alcohol, such as p-nitrophenol, N-hydroxybenzotriazole (HOBt), N-hydroxysuccinimide or OPfp (pentafluorophenol).

Alternatively, the reagent VIII used for the N-acylation may possess another common leaving group W, for example thiophenyl or imidazolyl.

The inventive N-acylations with the above-described reagents of the formula VIII can be carried out analogously to known processes.

Preference is given to using, for the N-acylation of compounds VI, carbonyl halides VIII, especially those in which the leaving group W is chlorine or bromine, and is more preferably chlorine. To this end, preferably from 0.5 to 4 mol and especially from 1 to 2 mol of the acid chloride are used per 1 mol of the compound VI.

Typically, the N-acylation of an aminobiphenyl VI is carried out with an acid chloride VIII in the presence of a base, for instance triethylamine, in which case generally from 0.5 to 10 mol, especially from 1 to 4 mol, of the base per 1 mol of the acid chloride are used.

Frequently, a compound of the formula VII will be prepared by initially charging the appropriate compound VI together with the base, preferably in a solvent, and adding the acid chloride stepwise, if appropriate dissolved in a solvent, at a temperature in the range from about −30° C. to 50° C., especially from 0° C. to 25° C. Typically, reaction is then allowed to continue at elevated temperature, for instance in the range from 0° C. to 150° C., especially from 15° C. to 80° C.

However, the acylation can also be carried out in the absence of a base. To this end, the acylation is performed in a biphasic system. In this case, one of the phases is aqueous and the second phase is based on at least one essentially water-immiscible organic solvent. Suitable aqueous solvents and suitable essentially water-immiscible organic solvents are described above and also in WO 03/37868. This reference, in which further suitable reaction conditions for acylation processes in the absence of bases are also described in general terms, is hereby fully incorporated by reference.

When at least one of the radicals R$^1$, R$^2$, R$^3$, R$^4$, R$^5$ and R$^7$ in compounds VI is an amino group, it is necessary for the selective preparation of compounds VII to protect this amino group before the acylation reaction, in order to prevent the acylation from proceeding on the nitrogen atom of this group. Suitable protecting groups and processes for introducing them are known to those skilled in the art. For example, the compound VI can be converted by reaction with Boc anhydride to a compound VI in which the respective radical R$^1$, R$^2$, R$^3$, R$^4$, R$^5$ or R$^7$ is NHR$^x$ in which Rx is tert-butoxycarbonyl.

The compound (VI) can be converted by reaction with acetyl chloride to a compound VI in which the respective radical R$^1$, R$^2$, R$^3$, R$^4$, R$^5$ or R$^7$ is NHR$^x$ in which Rx is acetyl. The compound (VI) can be converted by reaction with dimethylformamide in the presence of POCl$_3$ or thionyl chloride to a compound VI in which the respective radical R$^1$, R$^2$, R$^3$, R$^4$, R$^5$ or R$^7$ is N=C—(CH$_3$)$_2$. The compound VI can be converted by reaction with allyl chloride to a compound VI in which the respective radical R$^1$, R$^2$, R$^3$, R$^4$, R$^5$ or R$^7$ is N(CH$_2$—CH=CH$_2$)$_2$. The compound VI can be converted by reaction with an aliphatic or aromatic aldehyde to a compound VI in which the respective radical R$^1$, R$^2$, R$^3$, R$^4$, R$^5$ or R$^7$ is N=C—R in which R is $C_1$-$C_3$-alkyl or aryl, such as phenyl. The compound VI can be converted by reaction with a $C_1$-$C_4$-alkyl- or arylsulfonyl chloride, especially with methylsulfonyl, to a compound VI in which the respective radical R$^1$, R$^2$, R$^3$, R$^4$ or R$^5$ is NHR$^x$ in which Rx is $C_1$-$C_4$-alkylsulfonyl or arylsulfonyl and especially methylsulfonyl. The compound VI can be converted by reaction with an alkylating agent, such as dimethyl sulfate, methyl iodide, methyl bromide, trimethyloxonium tetrafluoroborate or triethyloxonium tetrafluoroborate, to a compound VI in which the respective radical R$^1$, R$^2$, R$^3$, R$^4$, R$^5$ or R$^7$ is (NR$^x$R$^c$R$^z$)$^+$V$^-$ in which R$^x$, R$^c$ and R$^z$ are each $C_1$-$C_4$-alkyl, especially methyl or ethyl, and V$^-$ is a halide anion, sulfate or tetrafluoroborate. Since the introduction of the protecting group at the stage of the compound VI does not proceed selectively under some circumstances, it is more favorable in these cases to introduce the protecting group actually before the reduction step and thus to use a compound V in which the respective radical R$^1$, R$^2$, R$^3$, R$^4$, R$^5$ or R$^7$ is a protected amino group. The protecting group can then, if desired, on completion of the acylation step, be eliminated again by means of known processes, for example by hydrolysis or, in the case of allyl protecting groups, by reaction with a base in the presence of palladium and a nucleophile such as malonic acid.

The reaction mixture obtained in the acylation step is worked up and the compound of the formula VII is isolated in a customary manner, for example by an aqueous, extractive workup, by removing the solvent, for example under reduced pressure, or by a combination of these measures. Further purification can be effected, for example, by crystallization, distillation or by chromatography.

Processes A, B and C according to the invention allow preparation, with a low level of complexity and in good yields and selectivities, of 2-nitrobiphenyls (I) and of 2-aminobiphenyls VI which are suitable starting compounds for preparing the carboxamides VII derived therefrom.

Some of the compounds I are novel and likewise form part of the subject matter of the present invention.

Specifically, the invention relates to compounds of formula I, wherein R$^1$, R$^2$, R$^4$, R$^5$ and R$^7$ are as defined above and a is 1 or 2.

Specifically, the invention also relates to compounds of the formula I, wherein R$^1$ and R$^5$ are H, R$^2$, R$^3$ and R$^4$ are F, R$^7$ is as defined above and a is 0, 1 or 2, preferably 0.

The invention also relates to compounds of the formula II, wherein R$^1$, R$^2$, R$^4$, R$^5$ and R$^7$ are as defined above and a' is 0, 1 or 2, preferably 1 or 2.

The invention also relates to compounds of the formula II, wherein R$^7$ is as defined above, a' is 0, 1 or 2, preferably 0, and
R$^1$, R$^2$, R$^4$ and R$^5$ are H, and R$^3$ is Cl; or
R$^1$ and R$^5$ are H and, R$^2$, R$^3$ and R$^4$ are F; or
R$^1$, R$^2$ and R$^5$ are H and R$^3$ and R$^4$ are Cl.

In the above compounds of formula II according to the invention, X is preferably Cl or Br.

The invention also relates to compounds of the formula III, wherein $R^1$, $R^2$, $R^4$, $R^5$ and $R^7$ are as defined above and a' is 0, 1 or 2, preferably 1 or 2.

The invention also relates to compounds of the formula III, wherein $R^7$ is as defined above, a' is 0, 1 or 2, preferably 0, and
$R^1$, $R^2$, $R^4$ and $R^5$ are H, and $R^3$ is Cl; or
$R^1$ and $R^5$ are H and, $R^2$, $R^3$ and $R^4$ are F; or
$R^1$, $R^2$ and $R^5$ are H and $R^3$ and $R^4$ are Cl.

The invention furthermore relates to compounds of the formulae X.1 and X.2

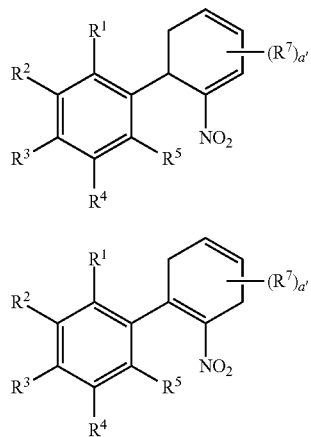

wherein $R^1$, $R^2$, $R^3$, $R^4$, $R^5$ and $R^7$ are as defined above and a' is 0, 1 or 2, preferably 1 or 2.

The invention also relates to compounds of the formulae X.1 and X.2, wherein $R^7$ is as defined above, a' is 0, 1 or 2, preferably 0, and
$R^1$, $R^2$, $R^4$ and $R^5$ are H, and $R^3$ is Cl; or
$R^1$ and $R^5$ are H and, $R^2$, $R^3$ and $R^4$ are F; or
$R^1$, $R^2$ and $R^5$ are H and $R^3$ and $R^4$ are Cl.

Compounds of formulae X.1 and X.2 are formed as intermediates if the aromatization in the elimination step (step (i) in processes B and C) does not take place concomitantly with the elimination. They are valuable intermediate products in the synthesis of compounds I, VI and VII.

The invention is further illustrated by the following, non-limiting examples.

EXAMPLES

1. Preparation of 4'-chloro-2-nitrobiphenyl

1.1 Preparation of p-chloro-β-nitrostyrene (1-chloro-4-(2-nitro-vinyl)-benzene)

To a solution of 57 g (98%, 0.397 mol) of 4-chlorobenzaldehyde and 24.8 g (0.398 mol) of nitromethane in 461 ml of toluene cooled to 5° C. were added 107.2 g of a solution of sodium methylate in methanol (30%; 0.596 mol) during 45 min. The mixture was subsequently stirred at 0 to 5° C. for 2 h. The suspension was cooled to 0° C. and then 40.0 g (0.666 mol) of anhydrous acetic acid were added, this causing the temperature to rise to 7° C. The mixture was diluted with 290 ml of toluene and methanol was removed by distillation at 100 mbar. 205 g (99%, 1.988 mol) of acetic anhydride were added, the mixture was heated to 50° C. and stirred for 15 h at this temperature. For workup, the mixture was poured onto 725 g of ice water, the phases were separated and the organic phase was extracted with alkaline water (pH 8.5). After concentration at 10 mbar, 74.8 g of the title compound in form of a yellow solid were obtained.

$^1$H-NMR (400 MHz, CD$_2$Cl$_2$): δ=7.94 (d, J=13.8 Hz, 1H), 7.59 (d, J=13.7 Hz, 1H), 7.50 (d, J=8.5 Hz, 2H), 7.41 (d, J=8.4 Hz, 2H) ppm.

$^{13}$C-NMR (125 MHz, CD$_2$Cl$_2$): δ=138.4, 138.0, 137.9, 130.8, 130.0, 129.1 ppm.

1.2 Preparation of 1-chloro-4-(6-nitrocyclohex-3-enyl)-benzene

Into a mixture of 5.7 g (30 mmol) of p-chloro-β-nitrostyrene from example 1.1 and 99 mg (0.9 mol) of hydroquinone in 25 ml of toluene were condensed 75 mmol of butadiene and the reaction mixture was stirred in an autoclave at 160° C. for 11 h. During reaction, pressure dropped from 6 bar to 4 bar. After completion of the reaction (monitored with HPLC, p-chlorophenyl-β-nitrostyrene content <1%) the reaction was depressurized, the solvent and excess butadiene were removed at 75° C. and 50 mbar and the residue was crystallized, yielding 7.3 g of a brown solid which was identified via HPLC to contain 97% of the title compound (yield: 95% of theory).

$^1$H-NMR (500 MHz, CD$_2$Cl$_2$): δ=7.31-7.26 (m, 2H), 7.21-7.16 (m, 2H), 5.82-5.76 (m, 1H), 5.74-5.69 (m, 1H), 4.97-3.89 (m, 1H), 3.42-3.35 (m, 1H), 2.79-2.72 (m, 2H), 2.51-2.42 (m, 1H), 2.35-2.25 (m, 1H) ppm.

$^{13}$C-NMR (125 MHz, CD$_2$Cl$_2$): δ=139.3, 133.6, 129.3, 129.3, 126.6, 123.1, 87.7, 44.2, 33.5, 31.6 ppm.

1.3 Preparation of 1-chloro-4-(6-halogeno-6-nitrocyclohex-3-enyl)-benzene

1.3.1 Preparation of 1-chloro-4-(6-bromo-6-nitrocyclohex-3-enyl)-benzene

A mixture of 1.8 g (7 mmol) of 1-chloro-4-(6-nitrocyclohex-3-enyl)-benzene from example 1.2 and 0.6 g (85%, 9.2 mmol) of KOH in 50 ml of methanol was stirred for 30 min at 25° C. under nitrogen atmosphere. A solution of 1.4 g (9 mmol) of bromine in 10 ml of methanol was added over a period of 3 min and the resulting mixture was stirred for 30 min at 25° C. The mixture was concentrated at 40° C. and 50 mbar, the resulting residue was mixed with dichloromethane (7 ml) and water (7 ml), the organic phase was separated and the solvent was evaporated at 40° C. and 50 mbar to yield 2.5 g of a yellow oil which was identified via HPLC to contain 90% of the title compound (yield: 95% of theory).

$^1$H-NMR (500 MHz, CD$_2$Cl$_2$): δ=7.26-7.20 (m, 4H), 6.04-5.98 (m, 1H), 5.85-5.78 (m, 1H), 4.00-3.95 (m, 1H), 3.25-3.09 (m, 2H), 3.07-2.99 (m, 1H), 2.65-2.57 (m, 1H) ppm.

$^{13}$C-NMR (125 MHz, CD$_2$Cl$_2$): δ=136.7, 134.6, 130.4, 129.3, 126.5, 122.8, 94.7, 48.1, 35.2, 32.4 ppm.

1.3.2 Preparation of 1-chloro-4-(6-chloro-6-nitrocyclohex-3-enyl)-benzene

A mixture of 0.45 g (1.8 mmol) of 1-chloro-4-(6-nitrocyclohex-3-enyl)-benzene from example 1.2 and 0.15 g (85%, 2.3 mmol) of KOH in 13 ml of methanol was stirred for 30 min at 25° C. under nitrogen atmosphere. 0.3 g (2.3 mmol) of N-chlorosuccinimide were added and the resulting mixture was stirred for 30 min at 25° C. The mixture was concentrated at 40° C. and 50 mbar, the resulting residue was mixed with dichloromethane (7 ml) and water (7 ml), the organic phase was separated and the solvent was evaporated at 40° C. and 50 mbar to yield 0.4 g of a yellow oil which was identified via HPLC to contain 94% of the title compound (yield: 69% of theory).

$^1$H-NMR (500 MHz, CD$_2$Cl$_2$): δ=7.26-7.18 (m, 4H), 6.02-5.96 (m, 1H), 5.83-5.77 (m, 1H), 3.20-3.12 (m, 1H), 3.08-2.99 (m, 2H), 2.90-2.82 (m, 1H), 2.60-2.52 (m, 1H) ppm.

$^{13}$C-NMR (125 MHz, CD$_2$Cl$_2$): δ=136.8, 134.7, 130.2, 129.3, 126.5, 122.6, 103.6, 47.9, 34.4, 31.5 ppm.

1.4 Preparation of 4'-chloro-2-nitrobiphenyl

To a solution of 0.55 g (1.75 mmol) of 1-chloro-4-(6-bromo-6-nitrocyclohex-3-enyl)-benzene from example 1.3.1 in 18.5 g of DMF were added 0.4 g (3.6 mmol) of potassium tert-butylate and 1.22 g (14 mmol) of MnO$_2$ and the resulting suspension was stirred for 6 h at 60° C. The mixture was concentrated at 80° C. and 50 mbar, the resulting residue was mixed with dichloromethane (25 ml) and water (25 ml), the organic phase was separated and washed with 10 ml of water and the solvent was evaporated at 40° C. and 50 mbar. The raw product was purified by flash chromatography (SiO$_2$, cyclohexane/ethylacetate 10:1) to yield 0.2 g of a brown viscous product which was identified via HPLC to contain 79% by weight of the title compound (yield: 38% of theory).

$^1$H-NMR (500 MHz, CD$_2$Cl$_2$): δ=7.89 (dd, J=8.0, 1.1 Hz, 1H), 7.66 (dt, J=7.6, 1.2 Hz, 1H), 7.56-7.51 (m, 1H), 7.46-7.40 (m, 3H), 7.30-7.25 (m, 2H) ppm.

2. Preparation of 3',4',5'-trifluoro-2-nitrobiphenyl

2.1 Preparation of 3,4,5-trifluoro-benzaldehyde

To a solution of 42.0 g (200 mmol) of 3',4',5'-trifluorobromobenzene in 200 ml of diethylether 88 ml of 2.5 M n-BuLi (220 mmol) were slowly added at −78° C. and the mixture was stirred for 30 min. Subsequently, 18.5 ml (230 mmol) of ethylformiate were added and the mixture was stirred for another 30 min at −78° C. After warming up to room temperature the solution was washed with water, the aqueous phase was extracted with dichloromethane and the organic phase was dried over Na$_2$SO$_4$. Approximately half of the solvent was then removed in vacuo.

2.2 Preparation of 3,4,5-trifluoro-β-nitrostyrene

To the raw product from example 2.1 were added 150 ml of acetic acid, 61.0 g (1.0 mol) of nitromethane and 26 g (340 mmol) of ammonium acetate and the mixture was heated to reflux for 3 h. After cooling to room temperature the resulting mixture was neutralized with aqueous NaOH (4M). The aqueous phase was extracted with 200 ml of dichloromethane, the organic phase was dried over Na$_2$SO$_4$ and the solvent was evaporated in vacuo. Column chromatography (SiO$_2$, pentane/diethylether 15:1) yielded 23 g (114 mmol, 57% of theory) of the title compound as a yellow solid, which was recrystallized from pentane/ethylacetate to give yellow crystals.

$^1$H-NMR (400 MHz, CDCl$_3$): δ=7.85 (d, 1H), 7.50 (d, 1H), 7.30-7.15 (m, 2H) ppm.

2.3 Preparation of 3,4,5-trifluoro-1-(6-nitrocyclohex-3-en-1-yl)-benzene 3.24 g (60 mmol) of butadiene were condensed at −78° C. into an autoclave under a nitrogen atmosphere. 2.03 g (10 mmol) of 3,4,5-trifluoro-β-nitrostyrene from example 2.2 dissolved in 6 ml of toluene and 30 mg of hydroquinone were added. A nitrogen atmosphere was applied (120 bar) and the suspension was heated for 12 h to 130° C. The reaction mixture was expanded and all volatiles were evaporated in vacuo. Column chromatography (SiO$_2$, cyclohexane/ethylacetate 9:1) yielded 2.4 g (9.4 mmol, 94% of theory) of the title compound as yellowish crystals.

$^1$H-NMR (400 MHz, CDCl$_3$): δ=6.95-6.85 (m, 2H), 5.85-5.70 (m, 2H), 5.90-4.80 (m, 1H), 3.45-3.35 (m, 1H), 2.75 (m, 2H), 2.55-2.45 (m, 1H), 2.30-2.20 (m, 1H) ppm.

2.4 Preparation of 3,4,5-trifluoro-1-(6-bromo-6-nitrocyclohex-3-en-1-yl)-benzene To a solution of 56 mg (1 mmol) of KOH in 6 ml of methanol was added dropwise a solution of 257 mg (1 mmol) of 3,4,5-trifluoro-1-(6-nitrocyclohex-3-en-1-yl)-benzene from example 2.3 in 4 ml of methanol/ethylacetate (3:1) and the resulting mixture was stirred for 20 min at room temperature. 178 mg (1 mmol) of NBS (N-bromosuccinimide) were added and the mixture was stirred for another 30 min. The solvents were evaporated in vacuo. Column chromatography (SiO$_2$, cyclohexane/ethylacetate 10:1) yielded 312 mg (0.93 mmol, 93% of theory) of the title compound as yellowish crystals.

$^1$H-NMR (400 MHz, CDCl$_3$): δ=7.00-6.90 (m, 2H), 6.10-6.00 (m, 1H), 5.90-5.80 (m, 1H), 4.00-3.90 (m, 1H), 3.30-3.05 (m, 3H), 2.70-2.50 (m, 1H) ppm.

2.5 Preparation of 3',4',5'-trifluoro-2-nitrobiphenyl

To a solution of 500 mg (1.49 mmol) of 3,4,5-trifluoro-1-(6-bromo-6-nitrocyclohex-3-en-1-yl)-benzene from example 2.4 in 10 ml of toluene were added 200 mg (0.6 mmol) of tetrabutylammonium bromide and 15 ml of aqueous NaOH (4M) and the mixture was stirred for 24 h at room temperature. During the reaction, air was sparged through the mixture. Then the reaction mixture was stirred for another 12 h at 50° C. After cooling to room temperature, the phases were separated, the aqueous phase was extracted with ethylacetate (3×10 ml) and the organic phases were dried over Na$_2$SO$_4$. Column chromatography (SiO$_2$, cyclohexane/ethylacetate 8:1) yielded 218 mg (0.86 mmol, 58% of theory) of the title compound as a reddish solid.

$^1$H-NMR (400 MHz, CDCl$_3$): δ=7.93 (d, 1H), 7.65 (t, 1H), 7.55 (t, 1H), 7.40 (d, 1H), 6.95 (t, 2H) ppm.

$^{13}$C-NMR (400 MHz, CDCl$_3$): δ=151.3, 148.9, 139.6, 135.1, 134.3, 133.3, 130.5, 127.5, 124.5, 113.8 ppm.

3. Preparation of 4'-chloro-2-aminobiphenyl

In a 20 ml autoclave were placed 1 g of xylene, 6 mg of a Pt/C catalyst (containing 1% by weight of Pt with respect to the weight of carbon) and 0.25 g (1 mmol) of 4'-chloro-2-nitrobiphenyl obtained in example 1.4. The mixture was stirred under hydrogen pressure (7-8 bar) at 100° C. until the starting material had disappeared (monitoring via HPLC). After completion of the reaction the mixture was cooled to ambient temperature and diluted with 15 ml of acetone. The catalyst was filtered off and the filtrate was evaporated in vacuo yielding 0.2 g (91% of theory) of the title compound in a purity of 93% (HPLC % by weight).

$^1$H-NMR (500 MHz, CD$_2$Cl$_2$): δ=7.42-7.37 (m, 4H), 7.15-7.09 (m, 1H), 7.08-7.03 (m, 1H), 6.80-6.70 (m, 2H), 3.73 (br s, 2H) ppm.

$^{13}$C-NMR (125 MHz, CD$_2$Cl$_2$): δ=144.1, 138.6, 133.3, 130.9, 130.6, 129.3, 129.2, 126.3, 118.9, 116.0 ppm.

We claim:
1. A process for preparing a compound of formula (I)

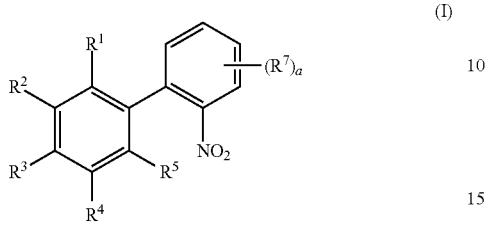

(I)

wherein
R$^1$, R$^2$, R$^3$, R$^4$ and R$^5$ are independently of each other selected from hydrogen; halogen; cyano; hydroxyl; C$_1$-C$_6$-alkyl, wherein the alkyl group may carry 1, 2 or 3 substituents R$^6$; C$_1$-C$_6$-haloalkyl; C$_3$-C$_{10}$-cycloalkyl which may carry 1, 2, 3 or 4 C$_1$-C$_4$-alkyl substituents; C$_3$-C$_{10}$-halocycloalkyl; C$_1$-C$_6$-alkoxy; C$_1$-C$_6$-haloalkoxy; C$_1$-C$_6$-alkylthio; C$_1$-C$_6$-haloalkylthio; aryl; aryl-C$_1$-C$_4$-alkyl; wherein aryl in the two last-mentioned radicals may carry 1, 2, 3 or 4 substituents selected from the group consisting of halogen, C$_1$-C$_4$-alkyl, C$_1$-C$_4$-haloalkyl and a radical R$^6$; amino; C$_1$-C$_4$-alkylamino; and di-(C$_1$-C$_4$-alkyl)-amino;
each R$^6$ is independently selected from the group consisting of C$_3$-C$_{10}$-cycloalkyl which may carry 1, 2, 3 or 4 C$_1$-C$_4$-alkyl substituents; C$_3$-C$_{10}$-halocycloalkyl; C$_1$-C$_4$-alkoxy; C$_1$-C$_4$-haloalkoxy; amino; C$_1$-C$_4$-alkylamino; di-(C$_1$-C$_4$-alkyl)-amino; carboxyl; hydroxyl; SH and aryl;
each R$^7$ is independently selected from the group consisting of C$_1$-C$_4$-alkyl, OR$^8$, amino, C$_1$-C$_4$-alkylamino, di-(C$_1$-C$_4$-alkyl)-amino and halogen;
wherein
R$^8$ is selected from the group consisting of hydrogen, C$_1$-C$_4$-alkyl, a protecting group, and aryl, wherein aryl may carry 1, 2, 3 or 4 substituents selected from the group consisting of halogen, C$_1$-C$_4$-alkyl, C$_1$-C$_4$-haloalkyl and a radical R$^6$; and
a is 0, 1 or 2;
comprising reacting a compound of formula (II)

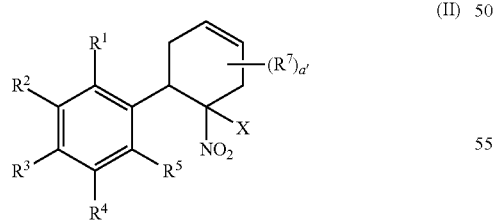

(II)

wherein a' is 0, 1 or 2 and X is a halogen atom,
wherein when a' is 2, the two substituent(s) R$^7$ are not bound to the same carbon atom, and wherein when a' is 1 or 2, the substituent(s) R$^7$ is/are not bound to the carbon atom carrying the phenyl substituent;
with a base wherein HX is eliminated from compound II in a dehydrohalogenation reaction,
and aromatizing the resulting product;

wherein aromatization is accomplished by carrying out the dehydrohalogenation reaction under air atmosphere and/or by keeping the reaction mixture at air atmosphere after the completion of the dehydrohalogenation; or by sparkling air or oxygen through the reaction mixture during the dehydrohalogenation reaction and/or after its completion; or by oxidizing the product of the dehydrohalogenation reaction with an oxidizing agent.
2. A process for preparing a compound of formula (VI)

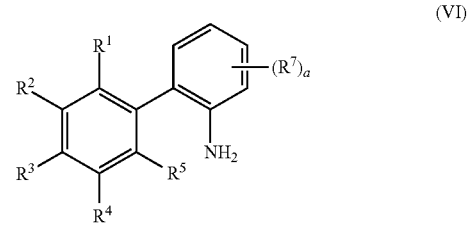

(VI)

wherein,
R$^1$, R$^2$, R$^3$, R$^4$ and R$^5$ are independently of each other selected from hydrogen; halogen; cyano; hydroxyl; C$_1$-C$_6$-alkyl, wherein the alkyl group may carry 1, 2 or 3 substituents R$^6$; C$_1$-C$_6$-haloalkyl; C$_3$-C$_{10}$-cycloalkyl which may carry 1, 2, 3 or 4 C$_1$-C$_4$-alkyl substituents; C$_3$-C$_{10}$-halocycloalkyl; C$_1$-C$_6$-alkoxy; C$_1$-C$_6$-haloalkoxy; C$_1$-C$_6$-alkylthio; C$_1$-C$_6$-haloalkylthio; aryl; aryl-C$_1$-C$_4$-alkyl; wherein aryl in the two last-mentioned radicals may carry 1, 2, 3 or 4 substituents selected from the group consisting of halogen, C$_1$-C$_4$-alkyl, C$_1$-C$_4$-haloalkyl and a radical R$^6$; amino; C$_1$-C$_4$-alkylamino; and di-(C$_1$-C$_4$-alkyl)-amino;
each R$^6$ is independently selected from the group consisting of C$_3$-C$_{10}$-cycloalkyl which may carry 1, 2, 3 or 4 C$_1$-C$_4$-alkyl substituents; C$_3$-C$_{10}$-halocycloalkyl; C$_1$-C$_4$-alkoxy; C$_1$-C$_4$-haloalkoxy; amino; C$_1$-C$_4$-alkylamino; di-(C$_1$-C$_4$-alkyl)-amino; carboxyl; hydroxyl; SH and aryl;
each R$^7$ is independently selected from the group consisting of C$_1$-C$_4$-alkyl, OR$^8$, amino, C$_1$-C$_4$-alkylamino, di-(C$_1$-C$_4$-alkyl)-amino and halogen; and
a is 0, 1 or 2;
comprising:
(i) preparing a compound of formula (I) according to the process of claim 1; and
(ii) reacting the compound of formula (I) with a reduction agent to obtain a compound of formula (VI).
3. A process for preparing a compound of formula (VII)

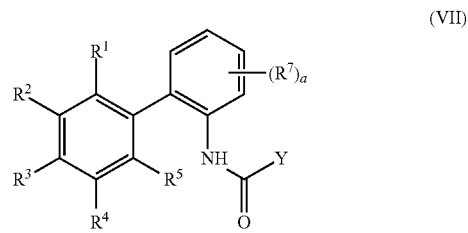

(VII)

wherein
R$^1$, R$^2$, R$^3$, R$^4$, R$^5$, R$^7$ are independently of each other selected from hydrogen; halogen; cyano; hydroxyl; C$_1$-C$_6$-alkyl, wherein the alkyl group may carry 1, 2 or 3 substituents R$^6$; C$_1$-C$_6$-haloalkyl; C$_3$-C$_{10}$-cycloalkyl which may carry 1, 2, 3 or 4 $C_1$-$C_4$-alkyl substituents; $C_3$-$C_{10}$-halocycloalkyl; $C_1$-$C_6$-alkoxy; $C_1$-$C_6$-haloalkoxl; $C_1$-$C_6$-alkylthio; $C_1$-$C_6$-haloalkylthio; aryl; aryl-$C_1$-$C_4$-alkyl; wherein aryl in the two last-mentioned radicals may carry 1, 2, 3 or 4 substituents selected from the group consisting of halogen, $C_1$-$C_4$-alkyl, $C_1$-$C_4$-haloalkyl and a radical $R^6$; amino; $C_1$-$C_4$-alkylamino; and di-($C_1$-$C_4$-alkyl)-amino;

each $R^6$ is independently selected from the group consisting of $C_3$-$C_{10}$-cycloalkyl which may carry 1, 2, 3 or 4 $C_1$-$C_4$-alkyl substituents; $C_3$-$C_{10}$-halocycloalkyl; $C_1$-$C_4$-alkoxy; $C_1$-$C_4$-haloalkoxy; amino; $C_1C_4$-alkylamino; di-($C_1$-$C_4$-alkyl)-amino; carboxyl; hydroxyl; SII and aryl;

each $R^7$ is independently selected from the group consisting of $C_1$-$C_4$-alkyl, $OR^8$, amino, $C_1$-$C_4$-alkylamino, di-($C_1$-$C_4$-alkyl)-amino and halogen;

a is 0, 1 or 2; and

Y is aryl or 5- or 6-membered hetaryl having 1, 2, 3 or 4 heteroatoms which are selected from the group consisting of N, O and S as ring members, where aryl and hetaryl optionally bear 1, 2, 3 or 4 substituents which are selected from the group consisting of halogen, $C_1$-$C_4$-alkyl, $C_1$-$C_4$-haloalkyl, $C_1$-$C_4$-alkoxy and $C_1$-$C_4$-haloalkoxy, comprising:
(i) preparing a compound of formula (VI) according to the process of claim 2; and
(ii) N-acylating the compound of the formula (VI) by reaction with a compound of the general formula (VIII),

(VIII)

wherein Y is as defined above; and
W is a leaving group.

4. The process as claimed in claim 3, where $R^1$, $R^2$, $R^3$, $R^4$ and $R^5$ are independently of each other selected from the group consisting of hydrogen, halogen, $C_1$-$C_6$-alkyl, $C_1$-$C_6$-haloalkyl, $C_1$-$C_6$-alkoxy and $C_1$-$C_6$-haloalkoxy.

5. The process as claimed in claim 4, where $R^1$, $R^2$, $R^3$, $R^4$ and $R^5$ are independently of each other selected from the group consisting of hydrogen and halogen.

6. The process as claimed in claim 5, wherein $R^1$ and $R^5$ are hydrogen.

7. The process as claimed in claim 6, where X is Cl or Br.

8. The process as claimed in claim 2, wherein $R^7$ in compounds of formulae I, VI and VII is methyl or dimethylamino and in compounds of formulae II, III and IX is methyl, dimethylamino or a group $OR^8$ wherein $R^8$ is selected from the group consisting of hydrogen, $C_1$-$C_4$alkyl, a protecting group, and aryl, wherein aryl may carry 1, 2, 3 or 4 substituents selected from the group consisting of halogen, $C_1$-$C_4$-alkyl, $C_1$-$C_4$-haloalkyl and a radical $R^6$; and each $R^6$ is independently selected from the group consisting of $C_3$-$C_{10}$-cycloalkyl which may carry 1, 2, 3 or 4 $C_1$-$C_4$alkyl substituents; $C_3$-$C_{10}$-halocycloalkyl; $C_1$-$C_4$-alkoxy; $C_1$-$C_4$-haloalkoxy; amino; $C_1$-$C_4$-alkylamino; di-($C_1$-$C_4$-alkyl)-amino; carboxyl; hydroxyl; SH and aryl.

9. The process as claimed in claim 3, wherein a in compounds of formulae I, VI and VII is 0 and a' in compounds of formulae II and III is 1 with $R^7$ being halogen.

10. The process as claimed in claim 9, where a is 0 and a' is 0 or 1.

11. The process as claimed in claim 3, where W is a halogen atom.

12. The process as claimed in claim 3, where Y is 5- or 6-membered hetaryl having 1, 2 or 3 nitrogen atoms as ring members, where the hetaryl optionally bears 1, 2 or 3 substituents which are selected from halogen, $C_1$-$C_4$alkyl and $C_1$-$C_4$haloalkyl.

13. The process as claimed in claim 12, where Y is selected from 2-chloropyrid-3-yl, 1-methyl-3-(trifluoromethyl)pyrazol-4-yl, 1-methyl-3-(difluoromethyl)pyrazol-4-yl and 1,3-dimethyl-5-fluoropyrazol-4-yl.

14. The process as claimed in claim 1, where the base is selected from the group consisting of inorganic bases which in turn are selected from the group consisting of alkali metal hydroxides, earth alkaline metal hydroxides, alkali metal carbonates and earth alkaline metal carbonates; and organic bases which in turn are selected from the group consisting of alkali metal $C_1$-$C_4$-alkoxides, aliphatic amines, basic, saturated, partially unsaturated or aromatic heteromono- or bicyclic rings containing at least one nitrogen ring atom and 5 to 10 ring members and cyclic amidines.

15. The process as claimed in claim 14, where the base is selected from inorganic bases and the reaction of the compound of formula (II) with the base is carried out in a biphasic solvent system comprising an organic solvent which is essentially immiscible with water, water and a phase transfer agent.

16. The process as claimed in claim 14, where the base is selected from organic bases and the reaction of the compound of formula (II) with the base is carried out in an organic solvent.

17. The process as claimed in claim 1, where the compound of formula (II) is obtained by reacting a compound of formula (III)

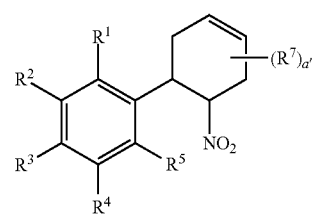
(III)

with a halogenating agent, wherein when a' is 2, the two substituents $R^7$ are not bound to the same carbon atom, and when a' is 1 or 2, the substituent(s) $R^7$ is/are not bound to the carbon atom carrying the phenyl substituent.

18. The process as claimed in claim 17, where the halogenating agent is selected from the group consisting of chlorine, bromine, N-chlorosuccinimide, N-bromosuccinimide and 1,3-dibromo-5,5-dimethyl hydantoine.

19. The process as claimed in claim 17, wherein the reaction of compound (III) with the halogenating agent is carried out in the presence of a base.

20. The process as claimed in claim 17, wherein the compound of formula (III) is obtained by reacting a compound of formula (IV)

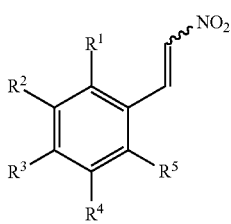

with butadiene or a butadiene derivative.

21. The process as claimed in claim 20, where the butadiene derivative is selected from sulfolene and a compound of formula IX

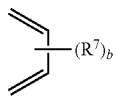

wherein b is 1 or 2 wherein when b is 2, the two substituents $R^7$ are not bound to the same carbon atom.

22. The process as claimed in claim 21, where the butadiene derivative is selected from the group consisting of sulfolene, isoprene, piperylene, 2,3-dimethyl-1,3-butadiene, butadiene, 1-methoxy-1,3-butadiene, 2-methoxy-1,3-butadiene, butadiene, 1-ethoxy-1,3-butadiene, 2-ethoxy-1,3-butadiene, 2,3-dimethoxy-1,3-butadiene, 1-dimethylamino-1,3-butadiene, 1-dimethylamino-3-trimethylsiloxy-1,3-butadiene and 1-dimethylamino-3-tert-butyldimethylsiloxy-1,3-butadiene.

23. The process as claimed in claim 21, wherein the butadiene derivative is butadiene.

24. The process as claimed in claim 21, wherein the compound of formula (IV) and butadiene or the butadiene derivative are reacted at a temperature of from 80 to 250 ° C.

25. The process as claimed in claim 21, wherein the compound of formula (IV) and butadiene or the butadiene derivative are reacted at a pressure of from 1 to 250 bar.

26. The process as claimed in claim 21, wherein the compound of formula (IV) is obtained by reacting a compound of formula (V)

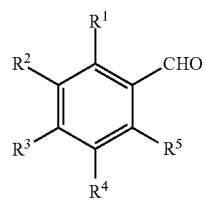

with nitromethane.

27. The process as claimed in claim 2, wherein the reduction in step (ii) is carried out by reacting the compound of formula (I) with hydrogen in the presence of a group VIII metal catalyst.

* * * * *